(12) United States Patent
Rubrecht et al.

(10) Patent No.: US 12,185,926 B2
(45) Date of Patent: Jan. 7, 2025

(54) QUICK CONNECT FOR ROBOTIC SURGERY

(71) Applicant: Orthosoft ULC, Montreal (CA)

(72) Inventors: Rodolphe Rubrecht, Liouc (FR);
Jeremie Menard, Montreal (CA);
Cornelius Hart, Montreal (CA);
Trong-Tin Nguyen, Laval (CA);
Delphine Cirette, Montreal (CA);
Alexis Balli, Montreal (CA);
Jean-Francois Girouard, Terrasse-Vaudreuil (CA)

(73) Assignee: Orthosoft ULC, Montreal (CA)

( * ) Notice: Subject to any disclaimer, the term of this patent is extended or adjusted under 35 U.S.C. 154(b) by 547 days.

(21) Appl. No.: 17/500,702

(22) Filed: Oct. 13, 2021

(65) Prior Publication Data

US 2022/0110616 A1 Apr. 14, 2022

Related U.S. Application Data

(60) Provisional application No. 63/091,563, filed on Oct. 14, 2020.

(51) Int. Cl.
*A61B 17/00* (2006.01)
*A61B 34/30* (2016.01)

(52) U.S. Cl.
CPC .............. *A61B 17/00* (2013.01); *A61B 34/30* (2016.02); *A61B 2017/00477* (2013.01)

(58) Field of Classification Search
CPC ..................... A61B 17/00; A61B 34/30; A61B 2017/00477

USPC .......................................................... 606/1
See application file for complete search history.

(56) References Cited

U.S. PATENT DOCUMENTS

| | | | |
|---|---|---|---|
| 8,038,683 B2 | 10/2011 | Couture et al. | |
| 8,211,041 B2 | 7/2012 | Fisher et al. | |
| 8,884,618 B2 | 11/2014 | Mahfouz | |
| 9,675,461 B2 | 6/2017 | Mahfouz | |
| 2016/0157941 A1* | 6/2016 | Anvari | A61B 34/70 279/143 |

(Continued)

FOREIGN PATENT DOCUMENTS

WO 2019139841 7/2019

OTHER PUBLICATIONS

"European Application Serial No. 21202517.5, Extended European Search Report mailed Mar. 11, 2022", 9 pgs.

(Continued)

*Primary Examiner* — Joseph M Dietrich
*Assistant Examiner* — Michael T. Holtzclaw
(74) *Attorney, Agent, or Firm* — SCHWEGMAN LUNDBERG & WOESSNER, P.A.

(57) ABSTRACT

Techniques for securing an instrument to a surgical robot are provided. In an example, an apparatus can include a first portion, a second portion and a collar. The first portion can attach to an end of an arm of the surgical robot and can include a first rod extending away from the arm. The second portion can hold the surgical instrument and can include a second rod extending away from the surgical instrument. The collar can slidably adjust along an aligned axis of the first and second portions secure interfaces of the portions and to allow engagement and dis-engagement of the interfaces with each other.

16 Claims, 22 Drawing Sheets

(56) References Cited

U.S. PATENT DOCUMENTS

| | | | |
|---|---|---|---|
| 2017/0312035 A1 | 11/2017 | May et al. | |
| 2018/0110576 A1* | 4/2018 | Kopp | A61B 34/71 |
| 2018/0126504 A1 | 5/2018 | Shelton, IV et al. | |
| 2019/0038281 A1 | 2/2019 | Shelton, IV et al. | |
| 2019/0117324 A1 | 4/2019 | Hibner et al. | |
| 2019/0231448 A1* | 8/2019 | McBrien | A61B 46/10 |
| 2022/0370157 A1 | 11/2022 | Malon et al. | |

OTHER PUBLICATIONS

"European Application Serial No. 21202517.5, Response filed Oct. 20, 2022 to Extended European Search Report mailed Mar. 11, 2022", 65 pgs.

U.S. Appl. No. 17/749,102, filed May 19, 2022, Robotic Knee Replacement Procedure and Instruments.

* cited by examiner

QUICK CONNECT FOR ROBOTIC SURGERY

CLAIM OF PRIORITY

This application claims the benefit of U.S. Provisional Patent Application Ser. No. 63/091,563, filed on Oct. 14, 2020, the benefit of priority of which is claimed hereby, and which is incorporated by reference herein in its entirety.

FIELD OF THE DISCLOSURE

The present document relates to robotic surgery techniques, and more particularly, to techniques for connecting equipment to a surgical robot.

BACKGROUND OF THE DISCLOSURE

The use of robotics in surgery is on the rise. Total and partial knee arthroplasty surgeries are performed over half a million times a year in the United States. In some cases, the surgeries are performed with assistance from a surgical robot. During robotically assisted surgeries, instruments are installed on the robot to perform various functions. In some surgeries, an instrument installed on an arm of a surgical robot may be replaced with a different instrument. Such replacements are often planned to allow the robot to continue with a new functionality or to replace a component, such as a reamer in hip or shoulder arthroplasty, with a fresher component, such as similar reamer with a sharper blade. In general, efficient use of time during surgery can avoid complications, therefore, quick, accurate, and repeatable replacement of a robotic instrument can avoid surgical delays.

SUMMARY OF THE DISCLOSURE

Techniques for securing an instrument to a surgical robot are provided. In an example, an apparatus can include a first portion, a second portion and a collar. The first portion can attach to an end of an arm of the surgical robot and can include a first rod extending away from the arm. The second portion can hold the surgical instrument and can include a second rod extending away from the surgical instrument. The collar can slidably adjust along an aligned axis of the first and second portions secure interfaces of the portions and to allow engagement and dis-engagement of the interfaces with each other.

This section is intended to provide an overview of subject matter of the present patent application. It is not intended to provide an exclusive or exhaustive explanation of the invention. The detailed description is included to provide further information about the present patent application.

DETAILED DESCRIPTION

Examples of the present disclosure provide techniques for quick, accurate, and repeatable installation of a surgical instrument to an arm of a surgical robot. As mentioned above, time is of the essence during any surgical procedure and anything that slows down a procedure can cause adverse outcomes as well as delaying the surgeon in getting to the next patient. Robotic assistance is, at least in part, intended to shorten procedure times as well as improving accuracy and repeatability. If not developed and refined, robotic surgical assistance can lengthen procedure times. One area of particular difficulty identified by the inventors is the time it can take to change surgical instruments affixed to a robotic arm. As surgical robots need to maintain precise control of instruments, the interface between the robotic arm and any surgical instrument must also maintain a high degree of precision. Maintaining precise positioning and enabling quick instrument changes is one of the problems solved by the instrument interface, or quick connect, discuss herein.

Figure 1:
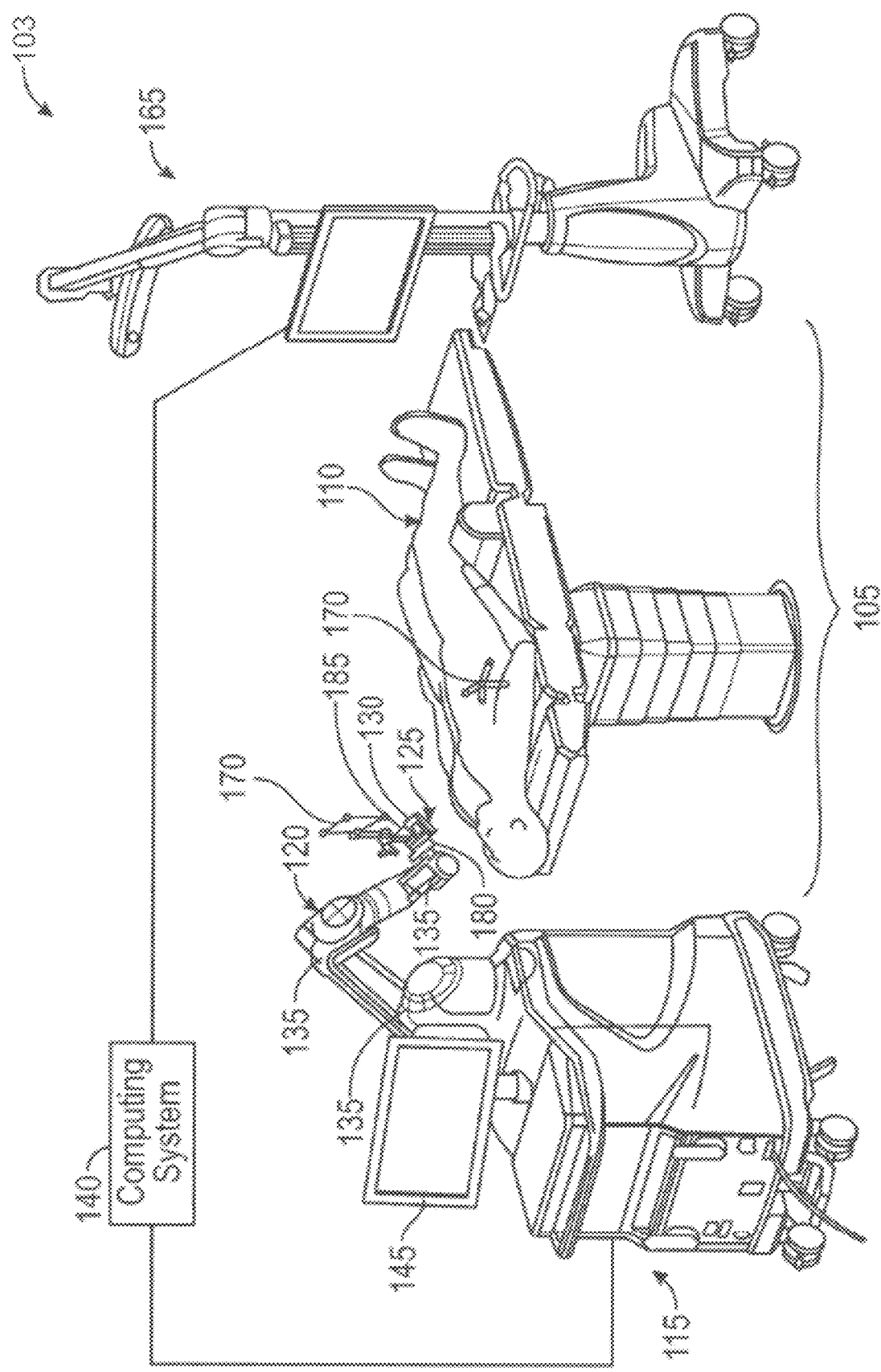
FIG. 1 is a diagrammatic view of an operating room including a robot-assisted surgical system comprising a robotic arm, a computing system and a tracking system.

FIG. 1 illustrates surgical system 103 for operation on surgical area 105 of patient 110 in accordance with at least one example of the present disclosure. Surgical area 105 in one example can include a joint and, in another example, can be a bone. Surgical area 105 can include any surgical area of patient 110, including but not limited to the shoulder, knee, head, elbow, thumb, spine, foot, ankle, and the like. Surgical system 103 can also include robotic system 115 with one or more robotic arms, such as robotic arm 120. As illustrated, robotic system 115 can utilize only a single robotic arm. Robotic arm 120 can be a 6 degree-of-freedom (DOF) robot arm, such as the ROSA® robot from Medtech, a Zimmer Biomet Holdings, Inc. company. In some examples, robotic arm 120 is cooperatively controlled with surgeon input on the end effector or surgical instrument, such as surgical instrument 125. In other examples, robotic arm 120 can operate autonomously. While not illustrated in FIG. 1, one or more positionable surgical support arms can be incorporated into surgical system 103 to assist in positioning and stabilizing instruments or anatomy during various procedures.

Each robotic arm 120 can rotate axially and radially and can receive a surgical instrument, or end effector, 125 at distal end 130. Surgical instrument 125 can be any surgical instrument adapted for use by the robotic system 115, including, for example, a guide tube, a holder device, a gripping device such as a pincer grip, a burring device, a reaming device, an impactor device such as a femoral or humeral head impactor, a pointer, a probe, a cutting guide, an instrument guide, an instrument holder or a universal instrument adapter device as described herein or the like. Surgical instrument 125 can be positionable by robotic arm 120, which can include multiple robotic joints, such as joints 135, that allow surgical instrument 125 to be positioned at any desired location adjacent or within a given surgical area 105. The surgical instrument 125 can be positioned directly by the robotic arm 120, or indirectly through positioning of a collar affixed to a quick connect as described herein, in which case the surgical instrument is directly manipulated in some other fashion, i.e. handheld.

Robotic system 115 can also include computing system 140 that can operate robotic arm 120 and surgical instrument 125. Computing system 140 can include at least memory, a processing unit, and user input devices, as will be described herein. Computing system 140 and tracking system 165 can also include human interface devices 145 for providing images for a surgeon to be used during surgery. Computing system 140 is illustrated as a separate standalone system, but in some examples computing system 140 can be integrated into robotic system 115. Human interface devices 145 can provide images, including but not limited to three-dimensional images of bones, glenoids, knees, joints, and the like. Human interface devices 145 can include associated input mechanisms, such as a touch screen, foot pedals, or other input devices compatible with a surgical environment.

Computing system 140 can receive pre-operative, intra-operative and post-operative medical images. These images can be received in any manner and the images can include, but are not limited to, computed tomography (CT) scans, magnetic resonance imaging (MRI), two-dimensional x-rays, three-dimensional x-rays, ultrasound, and the like. These images in one example can be sent via a server as files attached to an email. In another example the images can be stored on an external memory device such as a memory stick and coupled to a USB port of the robotic system to be uploaded into the processing unit. In yet other examples, the images can be accessed over a network by computing system 140 from a remote storage device or service.

After receiving one or more images, computing system 140 can generate one or more virtual models related to surgical area 105. Alternatively, computer system 140 can receive virtual models of the anatomy of the patient prepared remotely. Specifically, a virtual model of the anatomy of patient 110 can be created by defining anatomical points within the image(s) and/or by fitting a statistical anatomical model to the image data. The virtual model, along with virtual representations of implants, can be used for calculations related to the desired location, height, depth, inclination angle, or version angle of an implant, stem, acetabular cup, glenoid cup, total ankle prosthetic, total and partial knee prosthetics, surgical instrument, or the like to be utilized in surgical area 105. In another procedure type, the virtual model can be utilized to determine resection locations on femur and tibia bones for a partial knee arthroplasty. In a specific example, the virtual model can be used to determine a gap height for a posterior femoral resection relative to a proximally resected tibia. In another procedure type, the virtual model can be utilized to determine resection locations on a femoral head for a total hip arthroplasty. In another procedure type, the virtual model can be utilized to determine reaming and impaction locations on an acetabulum for a total hip arthroplasty. In another procedure type, the virtual model can be utilized to determine resection locations on a humeral head for a total shoulder arthroplasty. In another procedure type, the virtual model can be utilized to determine reaming and impaction locations on a glenoid or humerus for a total or reverse shoulder arthroplasty. The virtual model can also be used to determine bone dimensions, implant dimensions, bone fragment dimensions, bone fragment arrangements, and the like. Any model generated, including three-dimensional models, can be displayed on human interface devices 145 for reference during a surgery or used by robotic system 115 to determine motions, actions, and operations of robotic arm 120 or surgical instrument 125. Known techniques for creating virtual bone models can be utilized, such as those discussed in U.S. Pat. No. 9,675,461, titled "Deformable articulating templates" or U.S. Pat. No. 8,884,618, titled "Method of generating a patient-specific bone shell" both by Mohamed Rashwan Mahfouz, as well as other techniques known in the art.

Computing system 140 can also communicate with tracking system 165 that can be operated by computing system 140 as a stand-alone unit. Surgical system 103 can utilize the Polaris optical tracking system from Northern Digital, Inc. of Waterloo, Ontario, Canada. Additionally, tracking system 165 can comprise the tracking system shown and described in Pub. No. US 2017/0312035, titled "Surgical System Having Assisted Navigation" to Brian M. May, which is hereby incorporated by this reference in its entirety. Tracking system 165 can monitor a plurality of tracking elements, such as tracking elements 170, affixed to objects of interest to track locations of multiple objects within the surgical field. Tracking system 165 can function to create a virtual three-dimensional coordinate system within the surgical field for tracking patient anatomy, surgical instruments, or portions of robotic system 115. Tracking elements 170 can be tracking frames including multiple IR reflective tracking spheres, or similar optically tracked marker devices, such as the NavitrackER® reference markers from Orthosoft ULC, a Zimmer Biomet Holdings, Inc. company. In one example, tracking elements 170 can be placed on or adjacent one or more bones of patient 110. In other examples, tracking elements 170 can be placed on robot robotic arm 120, surgical instrument 125, and/or an implant to accurately track positions within the virtual coordinate system associated with surgical system 103. In each instance tracking elements 170 can provide position data, such as patient position, bone position, joint position, robotic arm position, implant position, or the like.

Robotic system 115 can include various additional sensors and guide devices. For example, robotic system 115 can include one or more force sensors, such as force sensor 180. Force sensor 180 can provide additional force data or information to computing system 140 of robotic system 115.

Force sensor 180 can be used by a surgeon to cooperatively move robotic arm 120. For example, force sensor 180 can be used to monitor impact or implantation forces during certain operations, such as insertion of an implant stem into a humeral or femoral canal. Monitoring forces can assist in preventing negative outcomes through force fitting components. In other examples, force sensor 180 can provide information on soft-tissue tension in the tissues surrounding a target joint. In certain examples, robotic system 115 can also include laser pointer 185 that can generate a laser beam or array that is used for alignment of implants during surgical procedures.

In order to ensure that computing system 140 is moving robotic arm 120 in a known and fixed relationship to surgical area 105 and patient 110, the space of surgical area 105 and patient 110 can be registered to computing system 140 via a registration process involving registering fiducial markers attached to patient 110 with corresponding images of the markers in patient 110 recorded preoperatively or just prior to a surgical procedure. For example, a plurality of fiducial markers can be attached to patient 110, images of patient 110 with the fiducial markers can be taken or obtained and stored within a memory device of computing system 140. Subsequently, patient 110 with the fiducial markers can be moved into, if not already there because of the imaging, surgical area 105 and robotic arm 120 can touch each of the fiducial markers. Engagement of each of the fiducial markers can be cross-referenced with, or registered to, the location of the same fiducial marker in the images. In additional examples, patient 110 and medical images of the patient can be registered in real space using contactless methods, such as by using a laser rangefinder held by robotic arm 120 and a surface matching algorithm that can match the surface of the patient from scanning of the laser rangefinder and the surface of the patient in the medical images. As such, the real-world, three-dimensional geometry of the anatomy attached to the fiducial markers can be correlated to the anatomy in the images and movements of instruments 125 attached to robotic arm 120 based on the images will correspondingly occur in surgical area 105.

Figure 2:
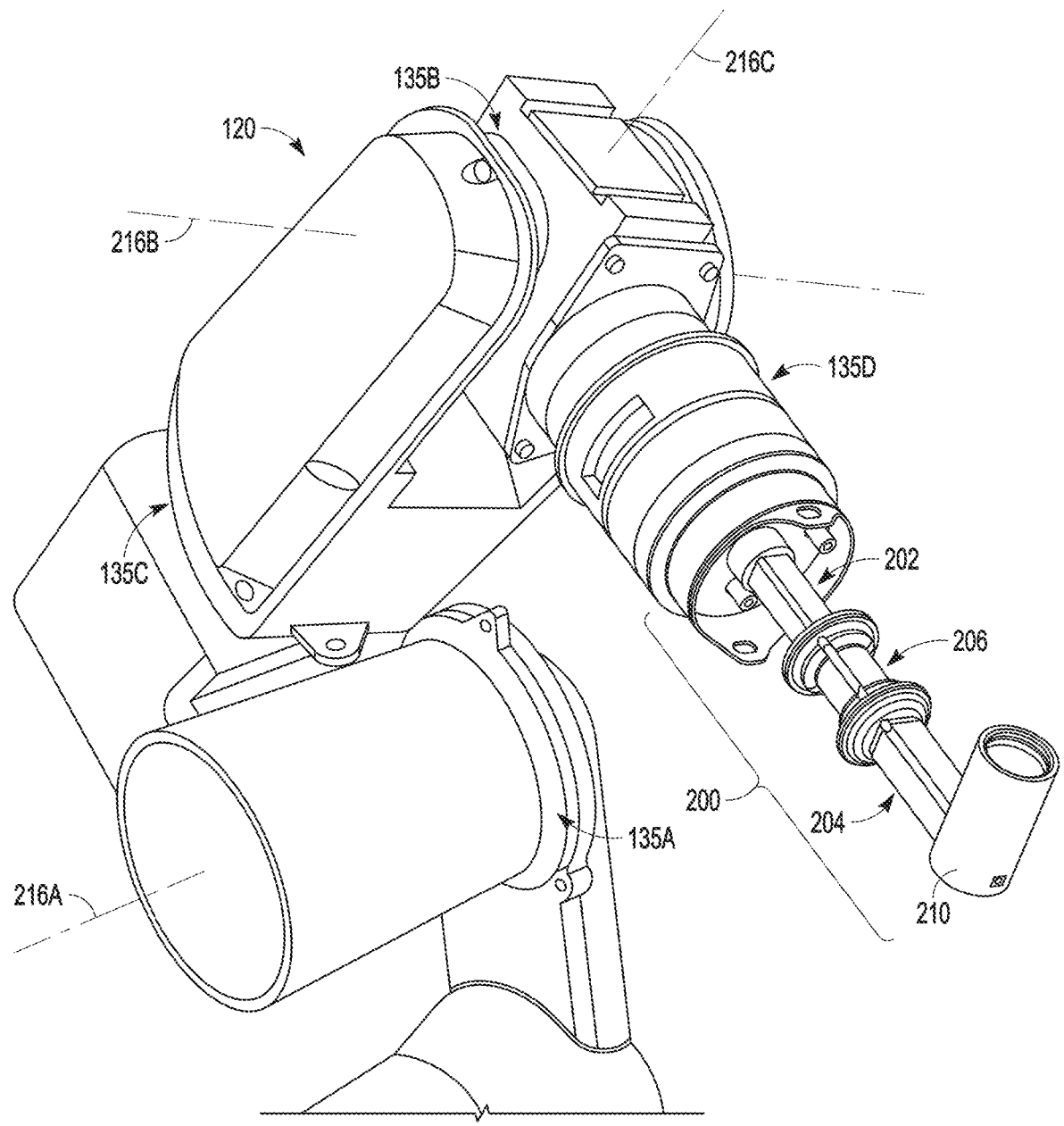
FIG. 2 is a schematic view of the robotic arm of FIG. 1 including a quick connect for easily connecting and disconnecting surgical instruments with the robotic arm.

FIG. 2 is a schematic view of robotic arm 120 of FIG. 1 including an example quick connect for quickly, accurately, and repeatably connecting and disconnecting a surgical instrument (not shown) with the robotic arm. In certain examples, the quick connect 200 can include a first portion 202, a second portion 204, and a collar 206. The surgical instrument can be coupled to the quick connect via a holder 210 of the second portion 204.

Figure 3:
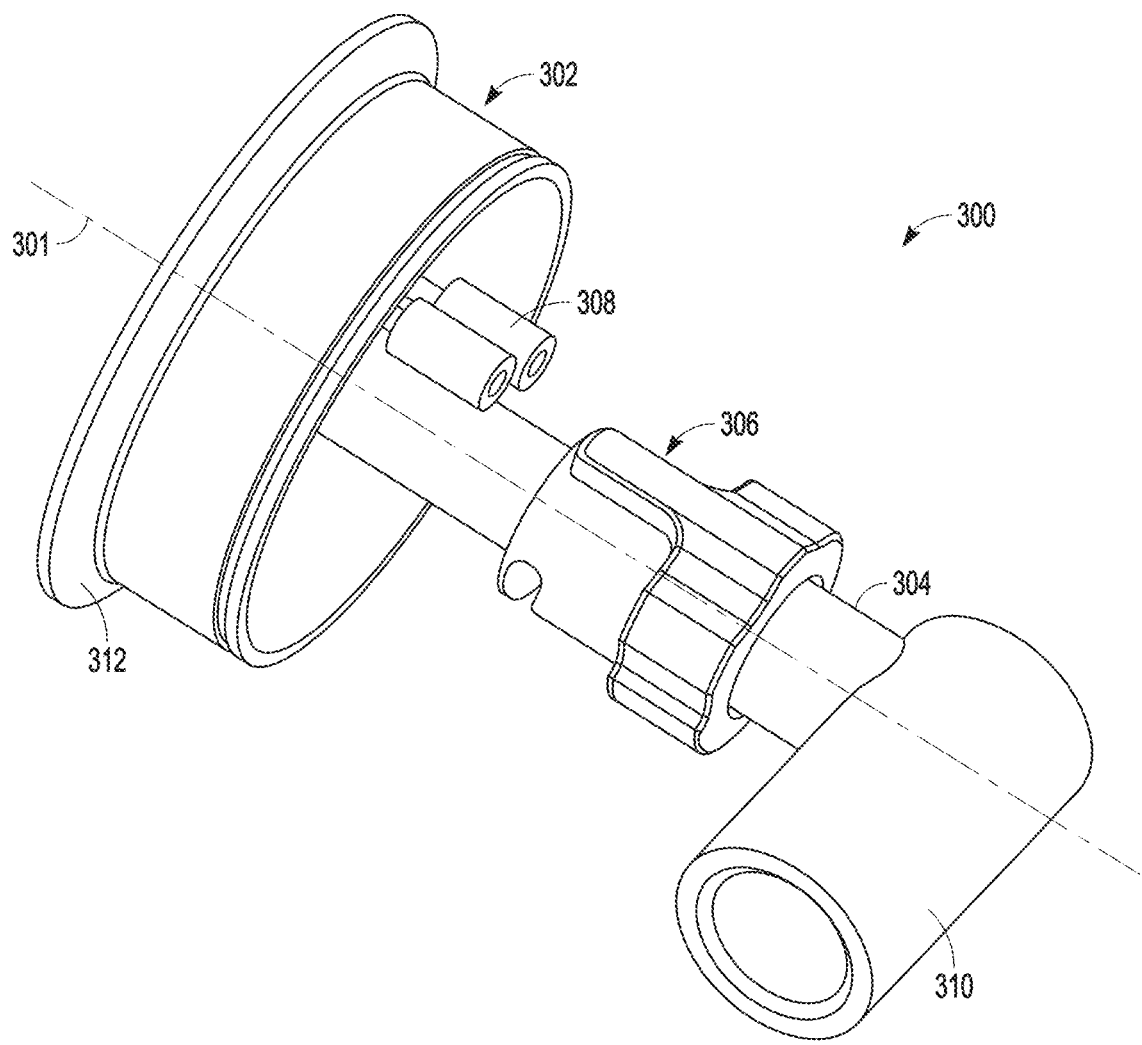
FIG. 3 illustrates generally an example quick connect for a surgical robot according to the present disclosure.

Robotic arm 120 can include joint 135A that permits rotation about axis 216A, joint 135B that can permit rotation about axis 216B, joint 135C that can permit rotation about axis 216C and joint 135D that can permit rotation about an axis of the end effector, such as axis 301 as shown in FIG. 3. To position the surgical instrument relative to anatomy of patient 110 (FIG. 1), surgical system 103 (FIG. 1) can manipulate robotic arm 120 automatically by computing system 140, or a surgeon manually operating computing system 140 to move the surgical instrument to the desired location, e.g., a location called for by a surgical plan to align an instrument relative to the anatomy. For example, robotic arm 120 can be manipulated along axes 216A-216C to position the surgical instrument to a desired location relative to the anatomy. Subsequent steps of the surgical procedure can be performed with other instruments by replacing the second portion 204 of the quick connect 200 with a new instrument assembled to a holder 210 of a different second portion.

FIG. 3 illustrates generally an example quick connect 300 for a surgical robot according to the present disclosure. The quick connect 300 can include a first portion 302, a second portion 304, and a collar 306. The first portion 302 of the quick connect 300 receives the second portion 304. The second portion 304 is locked into position on the first portion 302 through a camming action between a collar 306 and interface features on the distal end of the first portion 302. The first portion 302 can be attached to the end of an arm of the surgical robot. The illustrated example includes bolts 308 for fastening the first portion 302 to the arm of the surgical robot. The second portion 304 can include a holder 310 for holding a surgical instrument (not shown) that the surgical robot can manipulate to perform or assist a surgical procedure. The illustrated holder 310 is in a tubular form but may have other forms without departing from the scope of the present subject matter. The collar 306 can secure an interface of each of the first portion 302 and second portion 304 and may provide a connecting force that also assists in providing rigidity to the connection between the first portion 302 and the second portion 304.

Figure 4A:
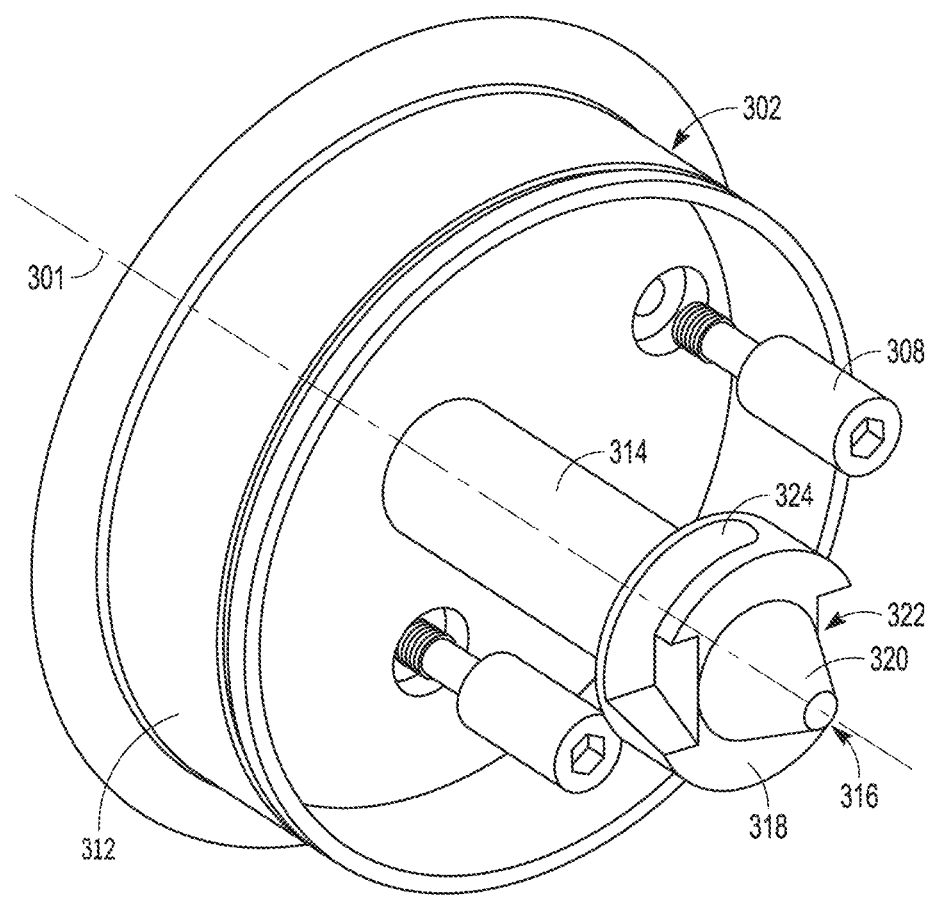
FIGS. 4A and 4B illustrate generally isolated views of the first portion of the example quick connect of FIG. 3.
Figure 4B:
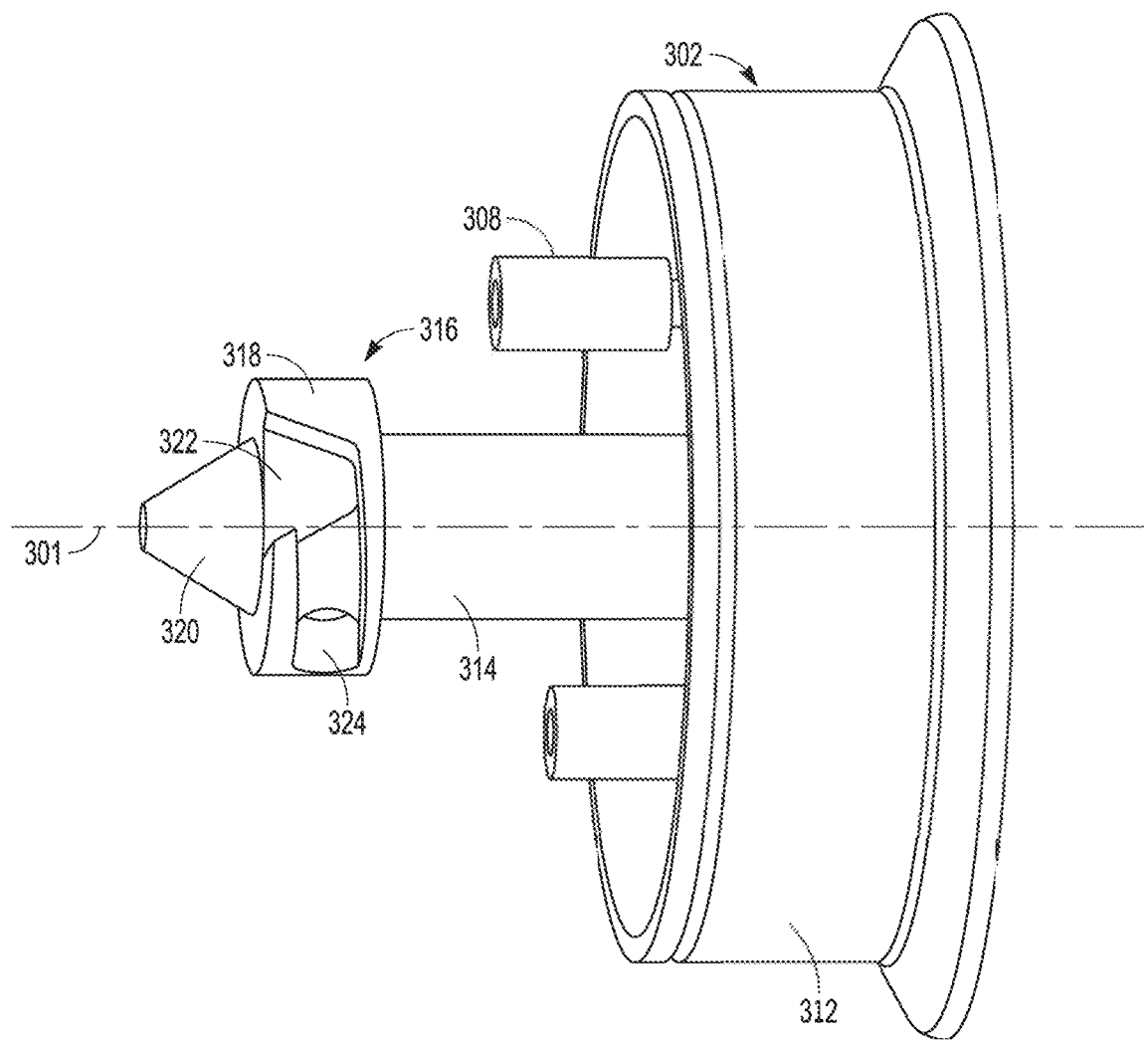

FIGS. 4A and 4B illustrate generally isolated views of the first portion 302 of the example quick connect 300 of FIG. 3. In certain examples, the first portion 302 can include a base 312, a rod 314, and an interface 316. The first portion 302 is intended to remain fixed to the surgical robot for an extended portion of a surgical procedure such that multiple instruments can be quickly connected and disconnected from the surgical robot as the procedure progresses. The base 312 supports the rod 314 and connects with the arm of the surgical robot using multiple fasteners 308. The rod 314 extends the arm of the surgical robot and connects the interface 316 with the base 312.

The interface 316 of the first portion 302 can be integrated with the rod 314 and can include a second collar 318, a first alignment feature 320 and a second alignment feature 322. In certain examples, the first alignment feature 320 can be on outward conical surface. Operation features of the first alignment feature 320 are discussed below with regard to the second portion 304 of the quick connect 300.

The second alignment 322 feature can include one or more inward notches positioned along a perimeter of the second collar 318 and extending parallel to a central axis of the interface 316 or the aligned axis 301 of the quick connect 300. The notches are designed to receive outward notches of the interface of the second portion 304 of the quick connect 300 such that the rotation orientation of the holder 310 with respect to the quick connect 300 is repeatable and accurate. Other alignment features are possible without departing for the scope of the present subject matter.

The second collar 318 can include one or more grooves 324. The one or more grooves 324 can guide a corresponding cam follow of the first collar (FIG. 3, 306) to allow the first collar to securely hold the interface of the first portion 302 with the interface of the second portion (FIG. 3, 304). For example, the grooves 324 of the second collar can allow the first collar to rotate about the central axis, or of the first alignment feature 320, or the aligned axis 301, while also allowing the first collar to pull or apply force to the second portion 304 toward the first portion 302. In certain examples, the first alignment feature 320 can be spring-loaded to allow an alignment surface of the first alignment feature 320 of the first portion 302 to maintain pressure against an alignment surface of the second portion 304 while also providing some "give" to allow the first collar 306 to fully rotate to the end of travel provided by the multiple grooves 324. In certain examples, the end of travel of the multiple grooves 324 may include a "detent" position that provides a tactile sensation to the user rotating the first collar 306. The tactile sensation may be provided by having a small relief at the end of the multiple grooves 324 that accepts the corresponding cam follower of the first collar 306. As the cam follower rotates into the relief, the end user may sense a "click" from the cam follower settling into the relief.

Figure 5:
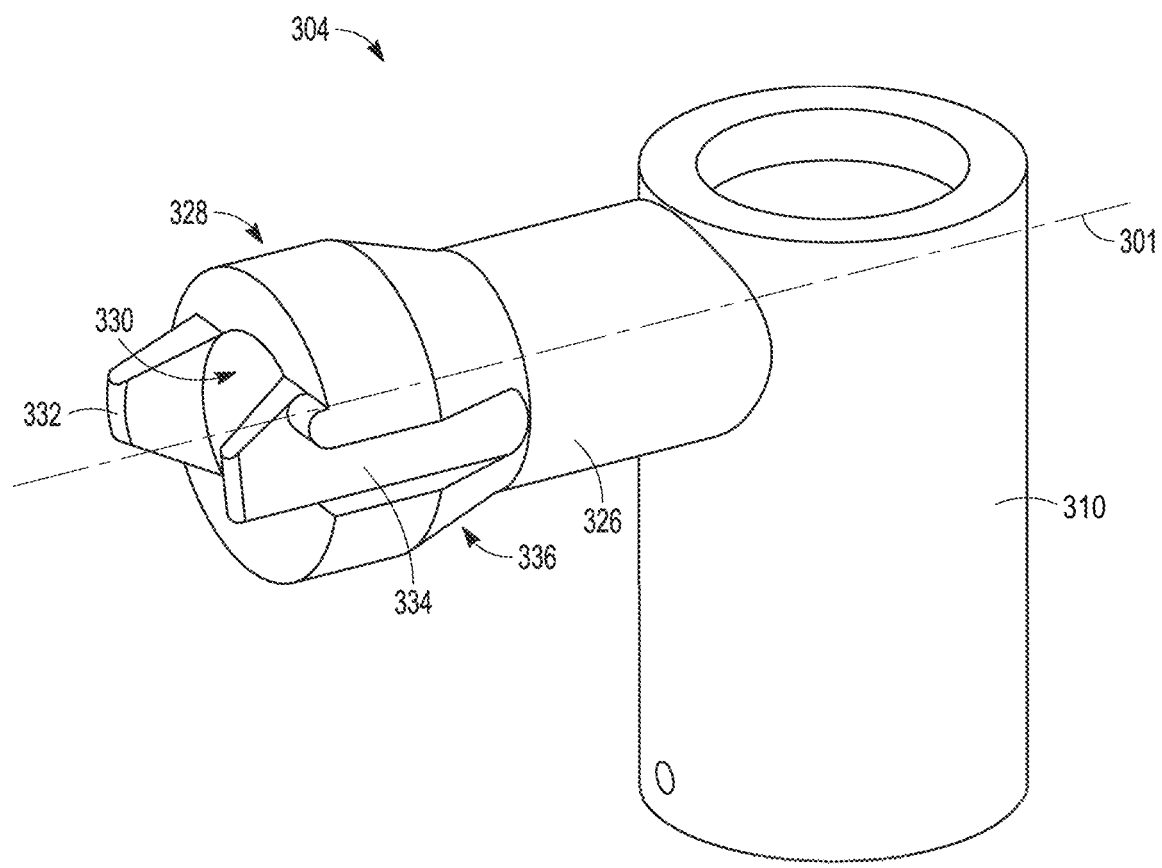
FIG. 5 illustrates generally an isolated view of the second portion of the quick connect of FIG. 3.

FIG. 5 illustrates generally an isolated view of the second portion 304 of the quick connect 300 of FIG. 3. The second portion 304 can include the holder 310, a rod 326, and an interface 328. As discussed above, the holder 310 secures a surgical instrument to the quick connect 300 that, in turn, allows the instrument to become an extension of the arm of the surgical robot. The interface 328 of the second portion aligns the second portion 304 with the first portion 302 for connection with the surgical robot and the rod 326 of the second portion couples the holder 310 with the interface 328 of the second portion. The interface 328 of the second portion includes a first alignment feature 330, a second alignment feature 332, multiple groves 334, and a thrust surface 336.

In the illustrated example, the first alignment feature 330 is an inward conical surface intended to receive and mate with the outward conical surface (FIG. 2, 320) of the first portion (FIGS. 3 and 4, 320). The mated conical surfaces 320, 330 of the first portion 302 and the second portion 304 of the quick connect can repeatedly and accurately align the rods 314, 326 of the first portion 302 and the second portion 304 along an aligned axis 301.

The second alignment feature 332 can include one or more outward notches positioned along a perimeter of the interface 328 and extending parallel to the central axis of the interface, or the aligned axis 301. The notches (e.g., 332) are designed to be received by inward notches of the interface of the first portion of the quick connect such that the rotational orientation of the holder 310 with respect to the quick connect is repeatable and accurate.

The multiple groves 334 of the interface of the second portion 304 allow the first collar (FIG. 3, 306) to be assembled with the second portion 304 prior to coupling the second portion 304 with the first portion. Upon assembly of the first portion with the second portion 304, the multiple grooves 334 of the second portion 304 can guide the cam followers of the first collar to the multiple grooves of the first portion 306 as the first collar is slid toward the first portion.

As the first collar 306 is rotated and the cam followers follow the groves of the first portion, the first collar 306 can be further displaced in the direction of the base of the first portion and a thrust surface of the first collar 306 can apply force to the thrust surface 336 of the interface 328 of the second portion 304 to draw the interface of the first portion together with the interface 328 of the second portion 304 and tightly secure the first portion with the second portion 304. The securing of the first and second portions of the quick connect via the rotation of the first collar provides rigidity of the assembled quick connect such that forces exerted at an angle to the aligned axis 301 of the quick connect, for example, via the surgical instrument, do not deflect the aligned axis 301 of the assembled quick connect, or are absorbed by or reflected back to the arm of the surgical robot.

Figure 6:
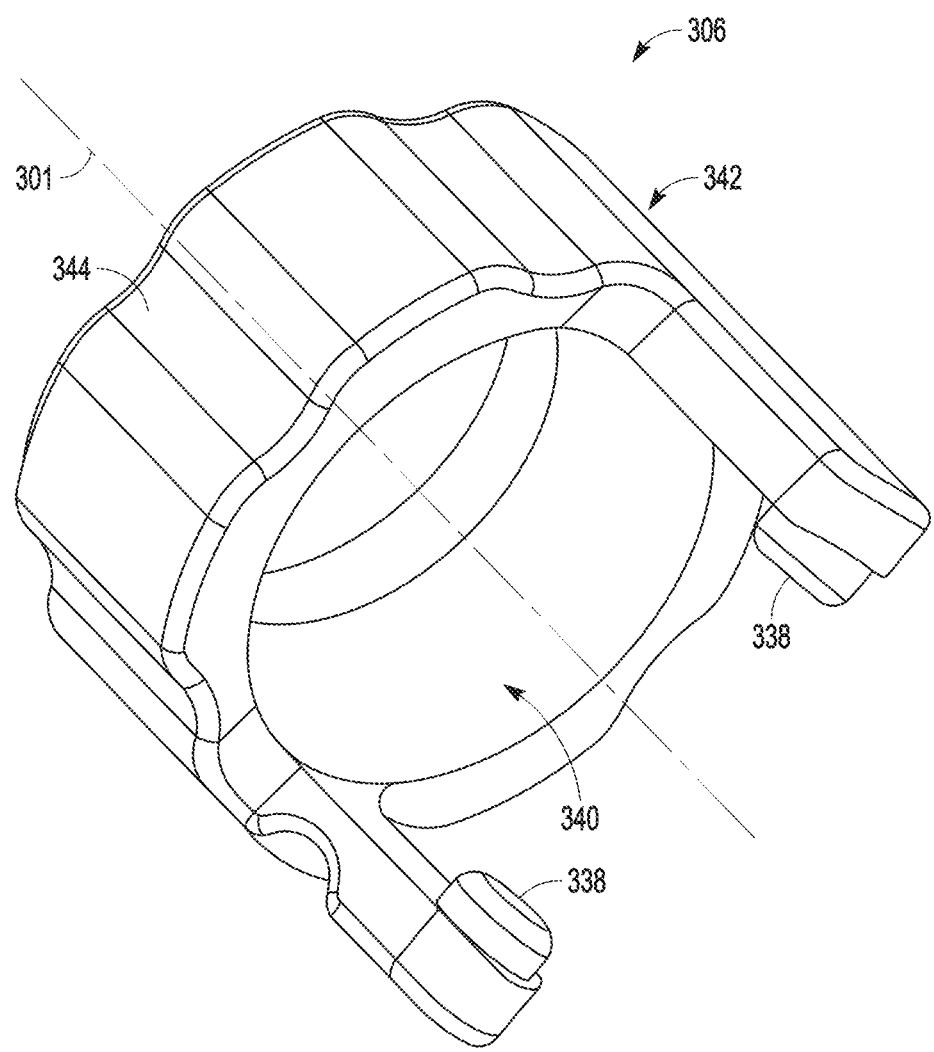
FIG. 6 illustrates generally the first collar of the example quick connect of FIG. 3.

FIG. 6 illustrates generally the first collar 306 of the example quick connect 300 of FIG. 3. The first collar 306 can include one or more cam followers 338 and a thrust surface 340. The first collar 306 can be ring shaped and is intended to be assembled to the second portion (FIG. 3, 304) of the quick connect before the second portion 304 is interfaced with the first portion (FIG. 1 302) of the quick connect. The one or more cam followers 338 are intended to be placed within and be guided by the grooves 324, 336 in each of the first portion 302 of the quick connect and the second portion 304 of the quick connect. When the interfaces of the first portion and the second portion are effectively engaged, the cam followers 338, when the first collar 306 is rotated, follow a ramped groove in the second collar of the first portion to pull the first and second portions together. The thrust surface 340 of the first collar 306 can be located on an inside wall of the first collar 306 and can engage the thrust surface (FIG. 5, 336) of the interface of the second portion of the quick connect to pull the first and second portions together when the first collar 306 is rotated. In certain examples, an exterior surface 342 of the first collar 306 can optionally include indentations 344 or knurling to provide a grip for a user to slide and rotate the first collar 306 of the quick connect.

Figure 7:
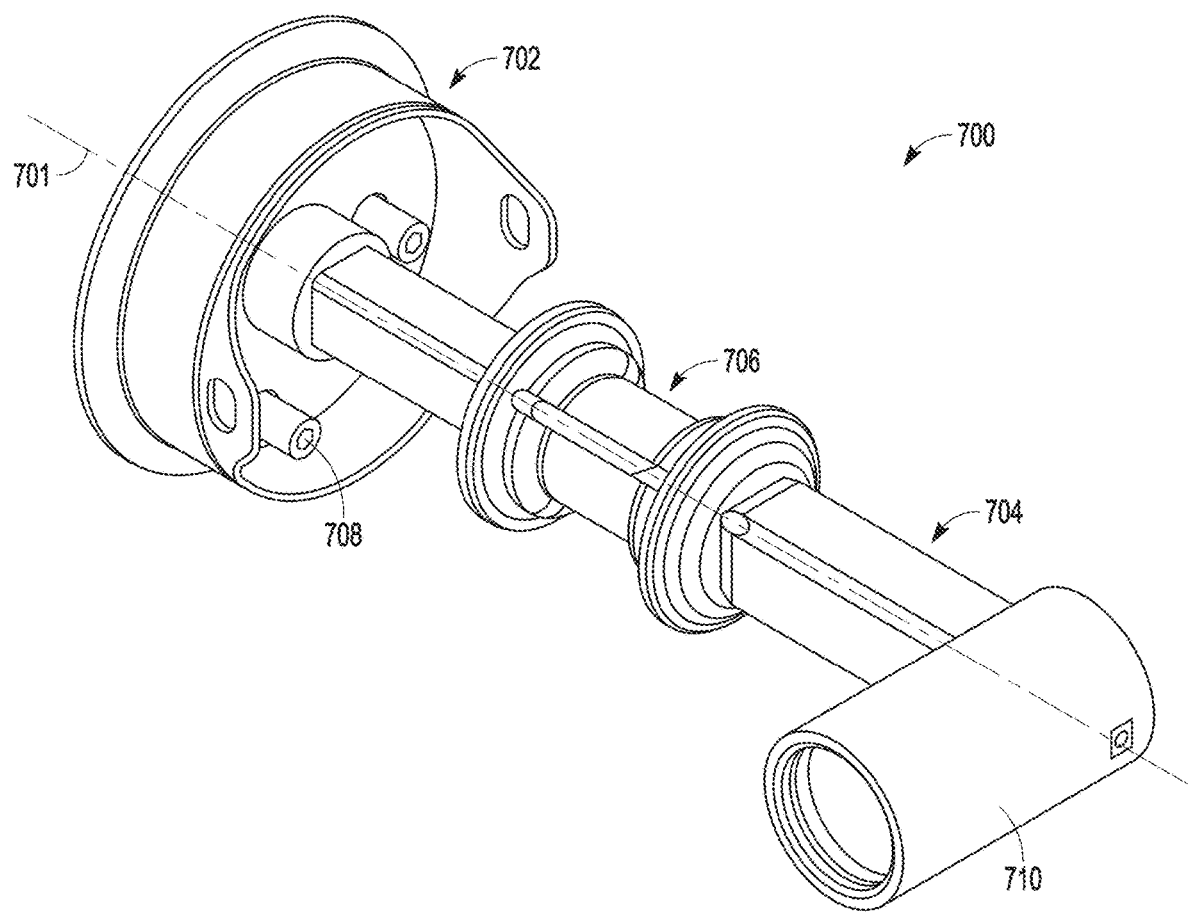
FIG. 7 illustrates generally an example quick connect for a surgical robot according to the present disclosure.

FIG. 7 illustrates generally an example quick connect 700 for a surgical robot according to the present disclosure. The quick connect 700 can include a first portion 702, a second portion 704, and a collar 706. The quick connect 700 operates by having the second portion 704 pivot into reception by the first portion 702 and the collar 706 is slid to secure the connection. For example, the collar 706 can be slid from an idle position about the first portion 702 to engage a thrust surface of the second portion 704 and cover the interface between the first and second portions 702, 704. The first portion 702 can be attached to the end of an arm of the surgical robot. The illustrated quick connect 700 includes bolts 708 for fastening the first portion 702 to the arm of the surgical robot. The second portion 704 can include a holder 710 for holding a surgical instrument that the surgical robot can manipulate to perform or assist a surgical procedure. The illustrated holder 710 is in a tubular form but may have other forms without departing from the scope of the present subject matter. The collar 706 can secure an interface of each of the first portion 702 and second portion 704 and may provide a connecting force that also assists in providing rigidity to the connection between the first portion 702 and the second portion 704.

Figure 8A:
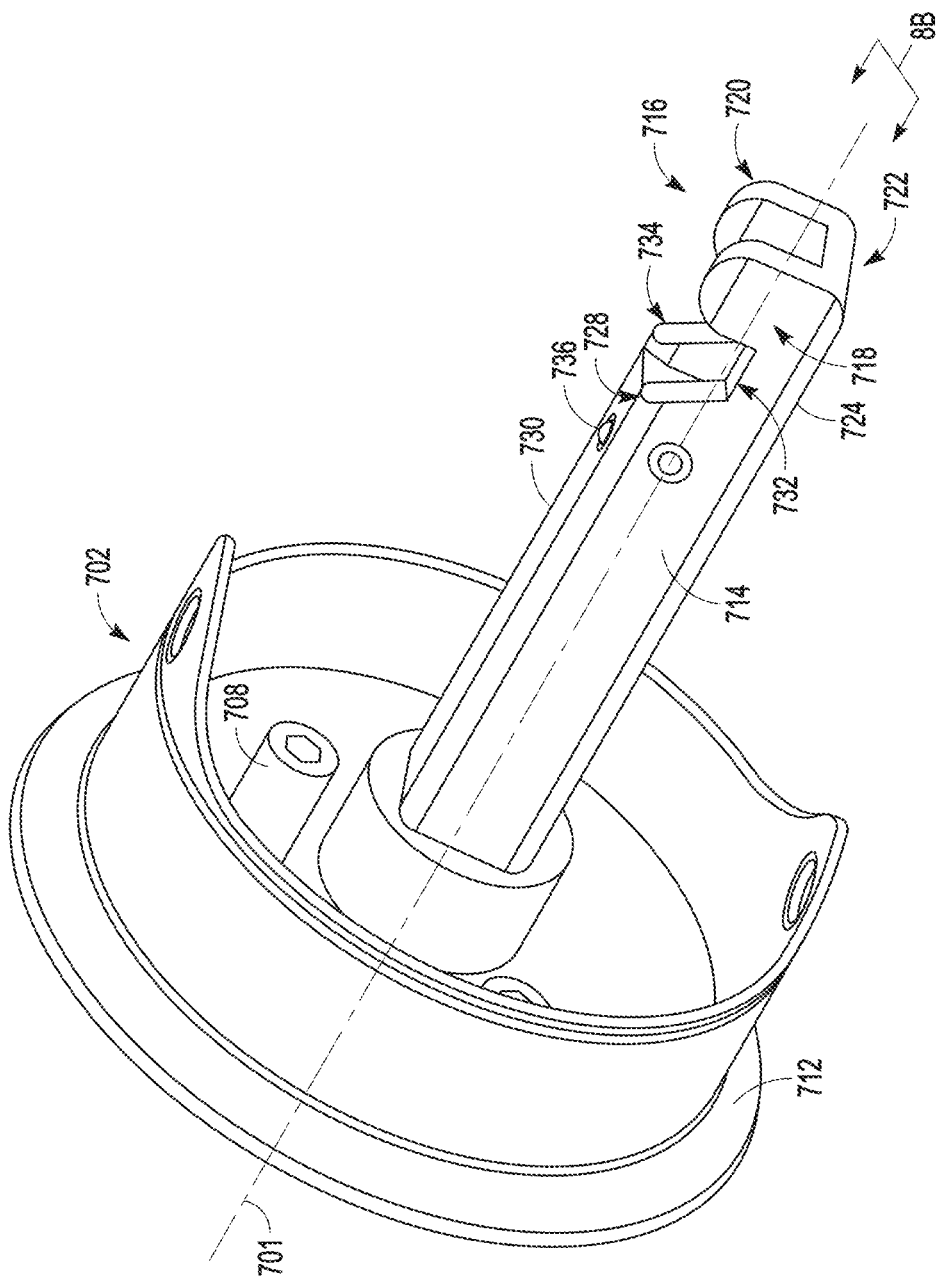
FIGS. 8A and 8B illustrate generally the first portion of the quick connect of FIG. 7.
Figure 8B:
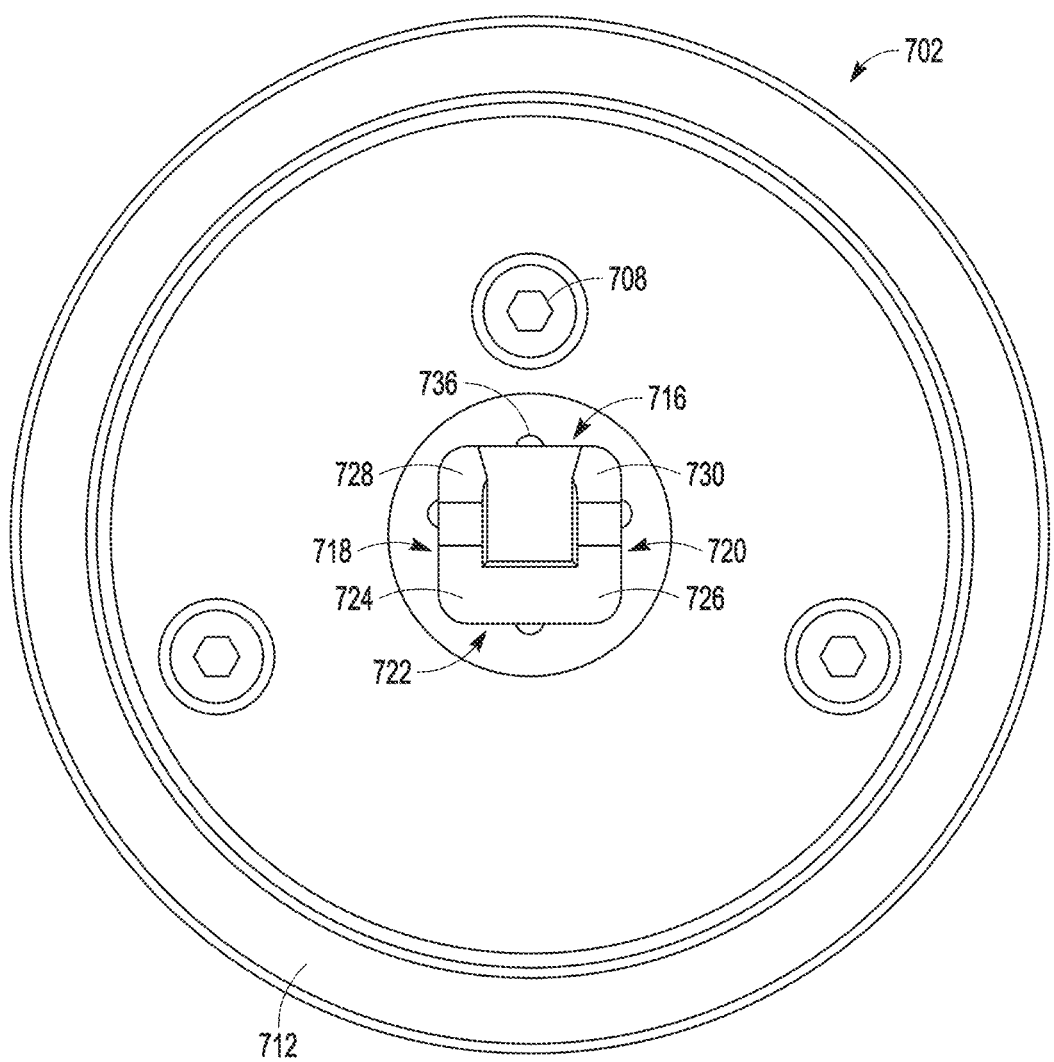

FIGS. 8A and 8B illustrate generally the first portion 702 of the quick connect 700 of FIG. 7. The first portion 702 can include a base, a rod, and an interface. The first portion 702 is intended to remain fixed to the surgical robot for an extended portion of a surgical procedure such that multiple instruments can be quickly connected and disconnected from the surgical robot as the procedure progresses. The base 712 supports the rod 714 and connects with the arm of the surgical robot using multiple fasteners 708. The rod 714 extends the arm of the surgical robot and connects the interface 716 with the base 712.

The interface 716 can be an extension of the rod 714. The interface can include a dual hook-shaped structure. For example, the interface 716 can include a first wall 718, a second wall 720, and a third or base wall 722. The first wall 718 and the second wall 720 can extend from the rod 714 and can be parallel with each other. The base wall 722 can extend from the rod 714 and can be joined with and between the first wall 718 and the second wall 720. The base wall 722 can further be joined with each of the first wall 718 and the second wall 720 along a first edge 724, 726 of each of the first wall 718 and the second wall 720. Along the second edge 728, 730 of each of the first wall 718 and the second wall 720, the interface can include a notch 732, 734. The notches 732, 734 form the hook ends of the hooks of the dual hook-shaped structure. As can be observed from the end view of FIG. 8B, the interface 716 can have a U-shaped cross-section.

In certain examples, the first portion can include multiple ball-detents 736 employed within the walls of the rod 714 proximate the interface 716. The ball detents include a spring-loaded ball. When the collar (FIG. 7, 706) is positioned to cover the interface 716, the ball detents 736 can apply pressure to align the collar 706 with the aligned axis 701 of the quick connect and to provide a holding force to resist displacing the collar 706 from its position.

Figure 9:
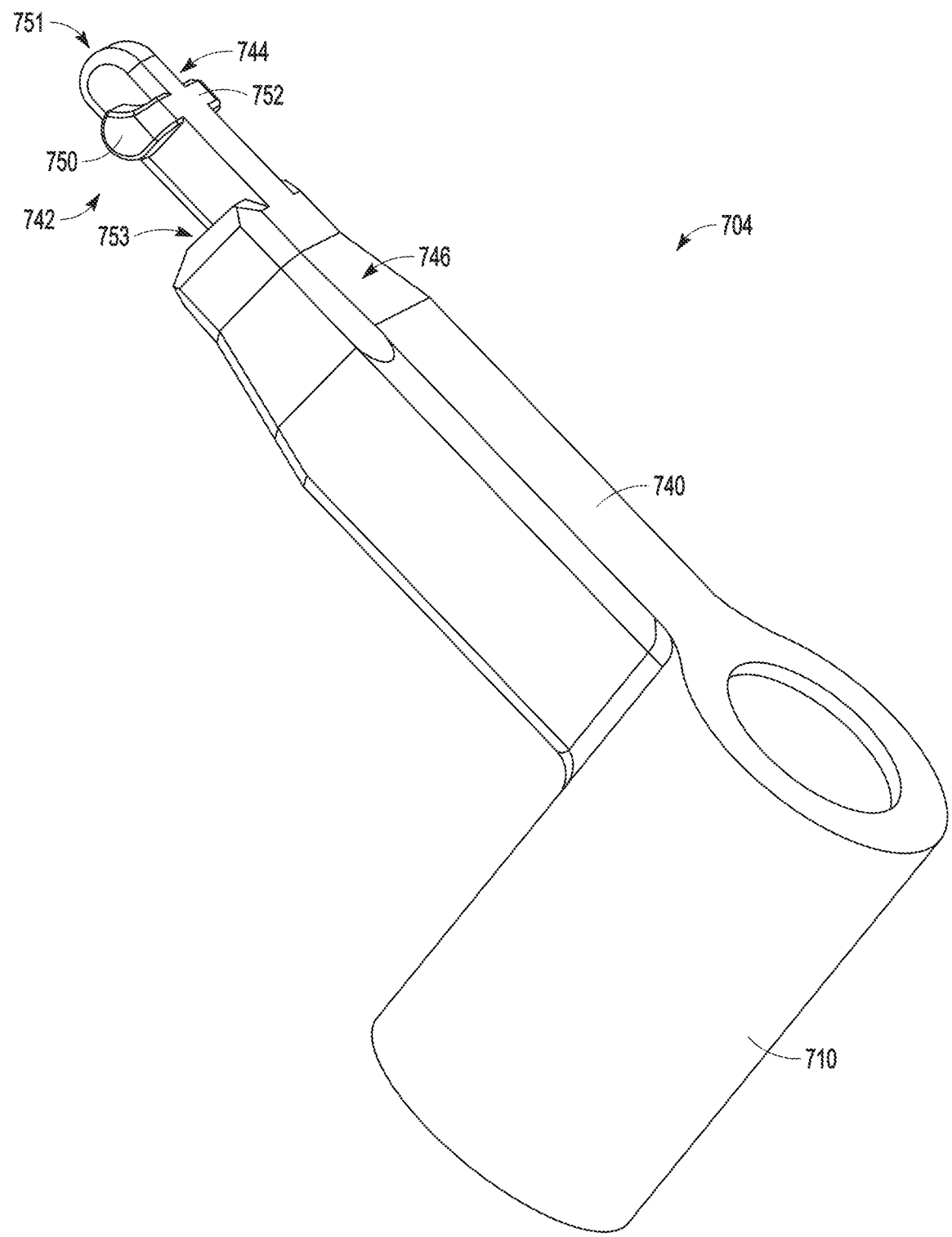
FIG. 9 illustrates generally an isolated view of the second portion of the quick connect of FIG. 7.

FIG. 9 illustrates generally an isolated view of the second portion 704 of the quick connect 700 of FIG. 7. The second portion 704 can include the holder 710, a rod 740, and an interface 742. As discussed above, the holder 710 secures a surgical instrument to the quick connect 700 that, in turn, allows the instrument to become an extension of the arm of the surgical robot. The interface 742 of the second portion 704 aligns the second portion 704 with the first portion 702 for connection with the surgical robot and the rod 740 of the second portion 704 can couple the holder 710 with the interface 742 of the second portion 704. The interface 742 of the second portion includes an alignment and coupling feature 744, and one or more alignment or thrust surfaces or areas 746.

The alignment and coupling feature 744 of the second portion 704 can include a post 748 extending from the end of the rod 740. A cross-section width of the post 748 in one direction can be much smaller than the corresponding cross-section width of the rod 740. A pair of nubs 750, 752 can extend from the post 748 to form a "t" shape. In certain examples, the pair of nubs 750, 752 do not extend from the post 748 at the distal end 751 of the post 748. In certain examples, the pair of nubs 750, 752 extend opposite each other from the post 748 at a location between the distal end 751 of the post 748 and the proximal end 753 of the post 748. In certain examples, the distal end 751 of the post 748 can be rounded.

Figure 10:
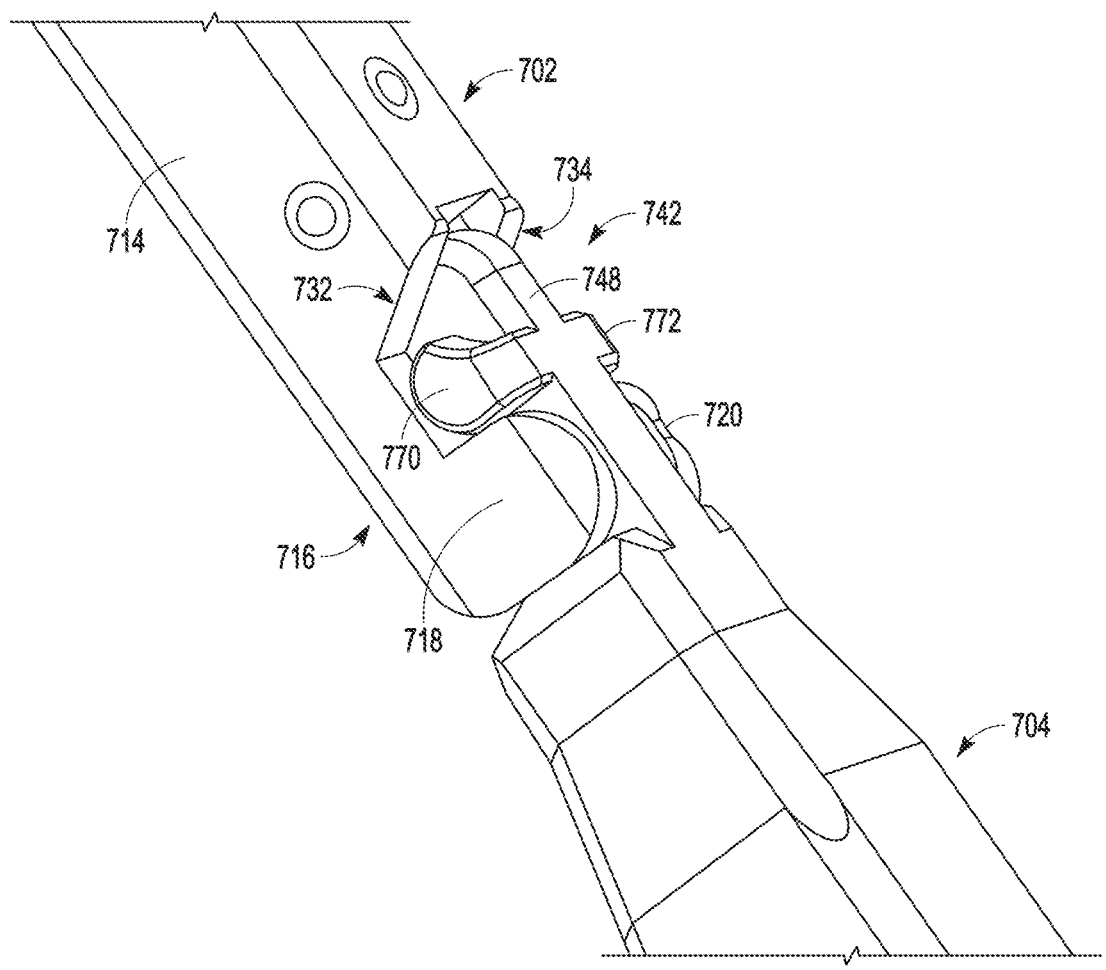
FIG. 10 illustrates generally the distal ends of the first portion of the quick connect and the second portion of the quick connect engaged with each other.

FIG. 10 illustrates generally the distal ends of the first portion 702 of the quick connect and the second portion 704 of the quick connect engaged with each other. In certain examples, the post 748 of the second portion is positioned between the first and second walls 718, 720 of the first portion 702 and the nubs 750, 752 of the second portion 704 rest in the notches 732, 734 of the first portion 702. In certain examples, when engaged with the hooks of the first portion, the nubs 750, 752 of the second portion 702 do not extend past the exterior surfaces of the first and second walls 718, 720 of the interface 716 of the first portion 702. In certain examples, engagement of the interfaces 716, 742 of the first and second portions 702, 704 of the quick connect limit the relative motion between the portions 702, 704. To complete the connection between the first portion 702 and the second portion 704, the collar (FIG. 7, 706) is slid from a position about the rod 714 of the first portion 702 to a lock position covering the interfaces 716, 742 of the first and second portions 702, 704.

Figure 11:
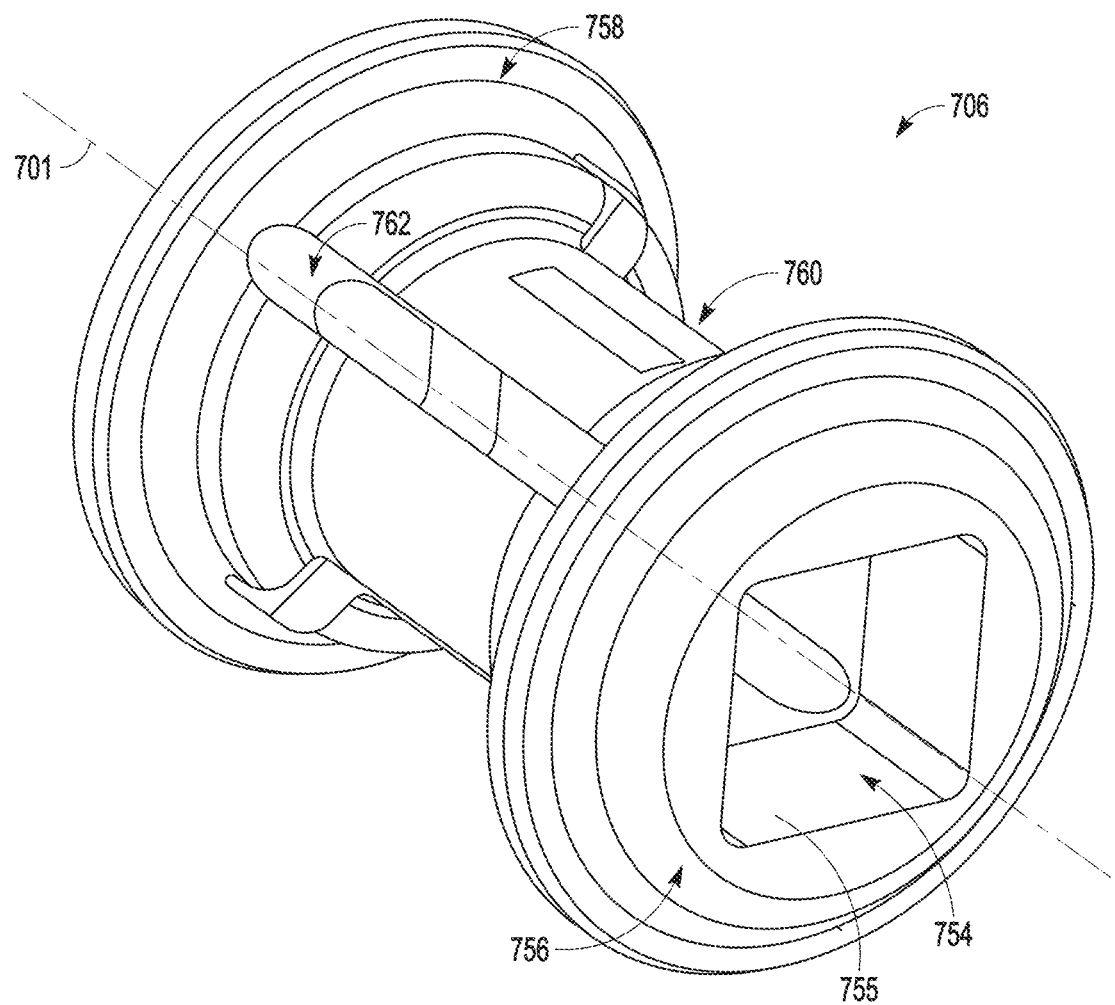
FIG. 11 illustrates generally an isolated view of the collar of the quick connect of FIG. 7.

FIG. 11 illustrates generally an isolated view of the collar 706 of the quick connect of FIG. 7. The collar 706 is tubular shaped with an internal passage 754 extending from a first end 756 to a second end 758. The end of the passage 754 or an opening of at least one of the first and second ends 756, 758 have one or more thrust alignment surfaces 755 shaped complementary to the shape of the rod (FIG. 9, 740) at the one or more alignment or thrust (FIG. 9, 746) area of the interface (FIG. 9, 742) of the second portion (FIG. 9, 704) of the quick connect (e.g., FIG. 7, 700). The outer surfaces of the collar 706 are generally circular. In certain examples, the outer portions of the collar 706 near at least one of the first or second ends 756, 758 have a larger diameter than a central portion 760 of collar 706. The larger diameters provide a surface for the user to exert pressure on the collar 706 to slide the collar 706 when assembled as part of the quick connect. In certain examples, the first end 756 of the collar 706 can be symmetrical or a mirror image with the second end 758 of the collar 706. Such a symmetrical configuration can allow the collar 706 to be assembled with the other portions without regard to whether the first end 756 of the collar 706 or the second end 758 of the collar 706 received the interface of the first end, for example. As such, the collar 706 can be assembled with the other portions of the quick connect in either of two ways which can reduce the amount of time compared to a collar that can only be assembled with the other portions with one particular end oriented in one particular direction. That is, the user does not need to observe an end of the collar to determine if that end can be properly assembled to the other portions first. Either end 756, 758 of the collar 706 can be assembled to the other portions first.

Figure 12:
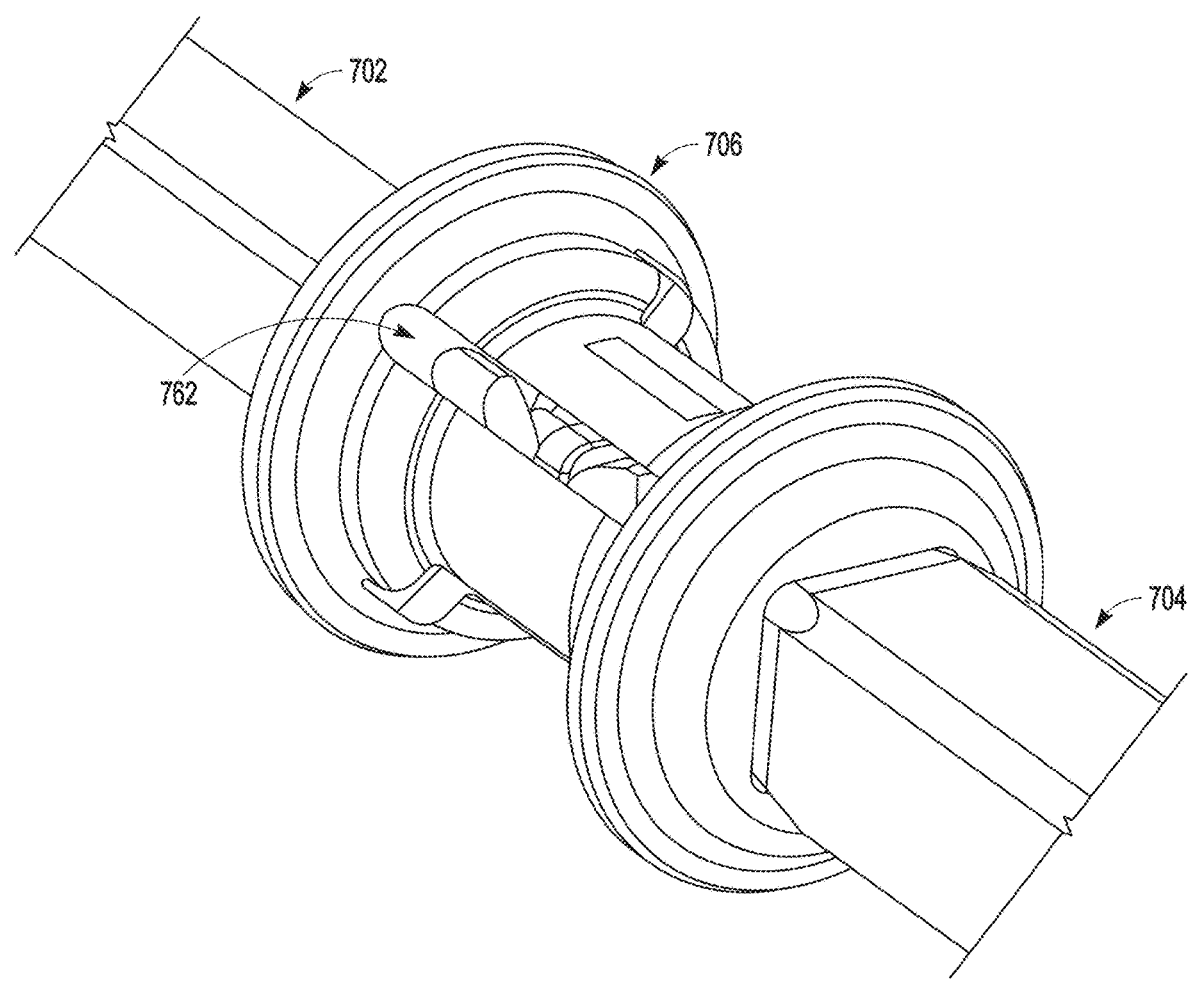
FIG. 12 illustrates generally a close-up view of assembled and securely connected interfaces of a quick connect according to the present subject matter.

In certain examples, the collar 706 can include one or more slots 762 oriented in parallel with the aligned axis 701. As can be observed in FIG. 10, the slots 762 can allow a user to observe the connection of the interfaces of the first portion 702 and the second portion 704 of the quick connect when the collar 706 is in a position to secure the connection of the interfaces of the first and second portions 702, 704 as illustrated in FIG. 12. FIG. 12 illustrates generally a close-up view of assembled and securely connected interfaces of a quick connect according to the present subject matter.

Figure 13A:
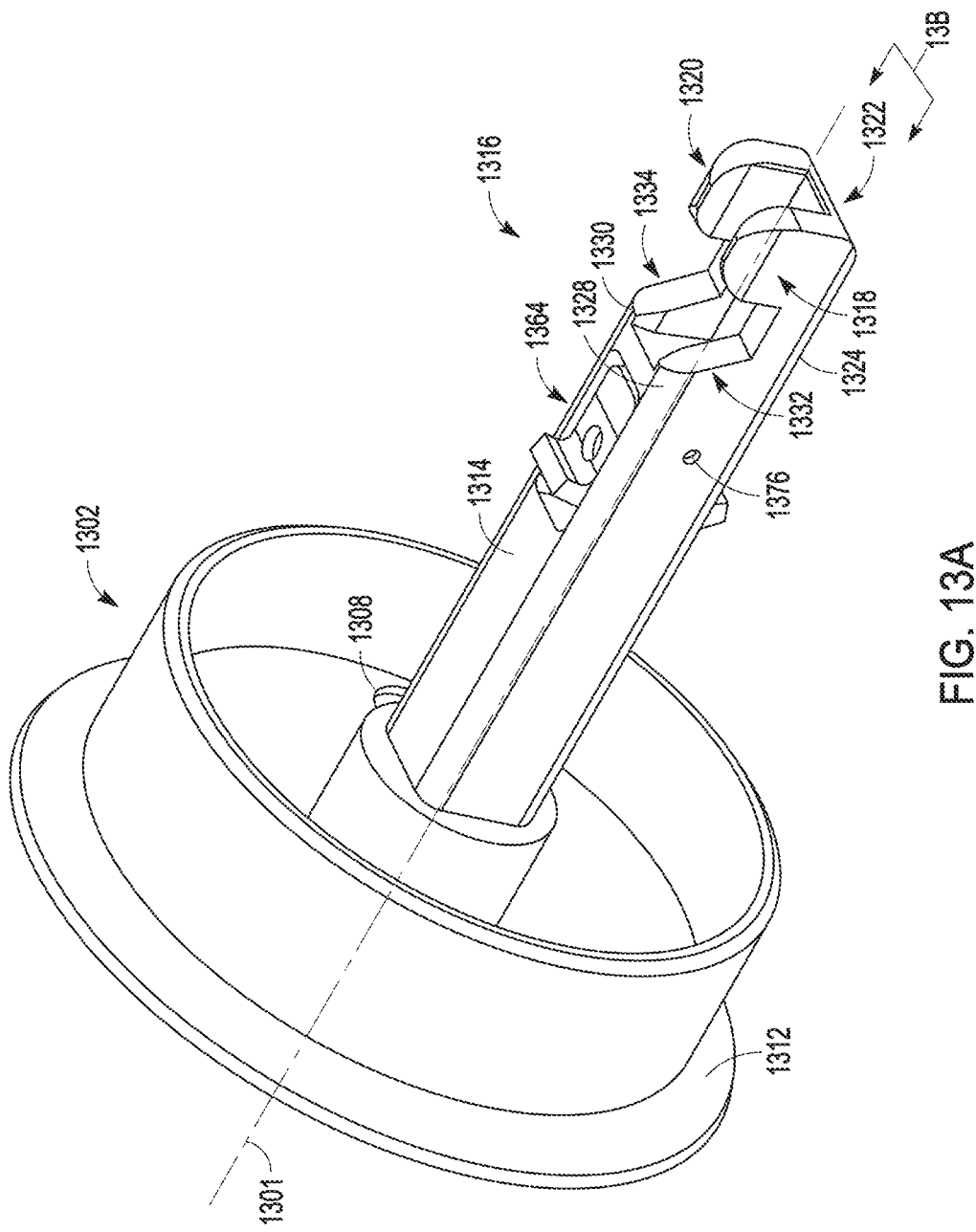
FIGS. 13A and 13B illustrate generally an alternative first portion for a quick connect according to the present subject matter.
Figure 13B:
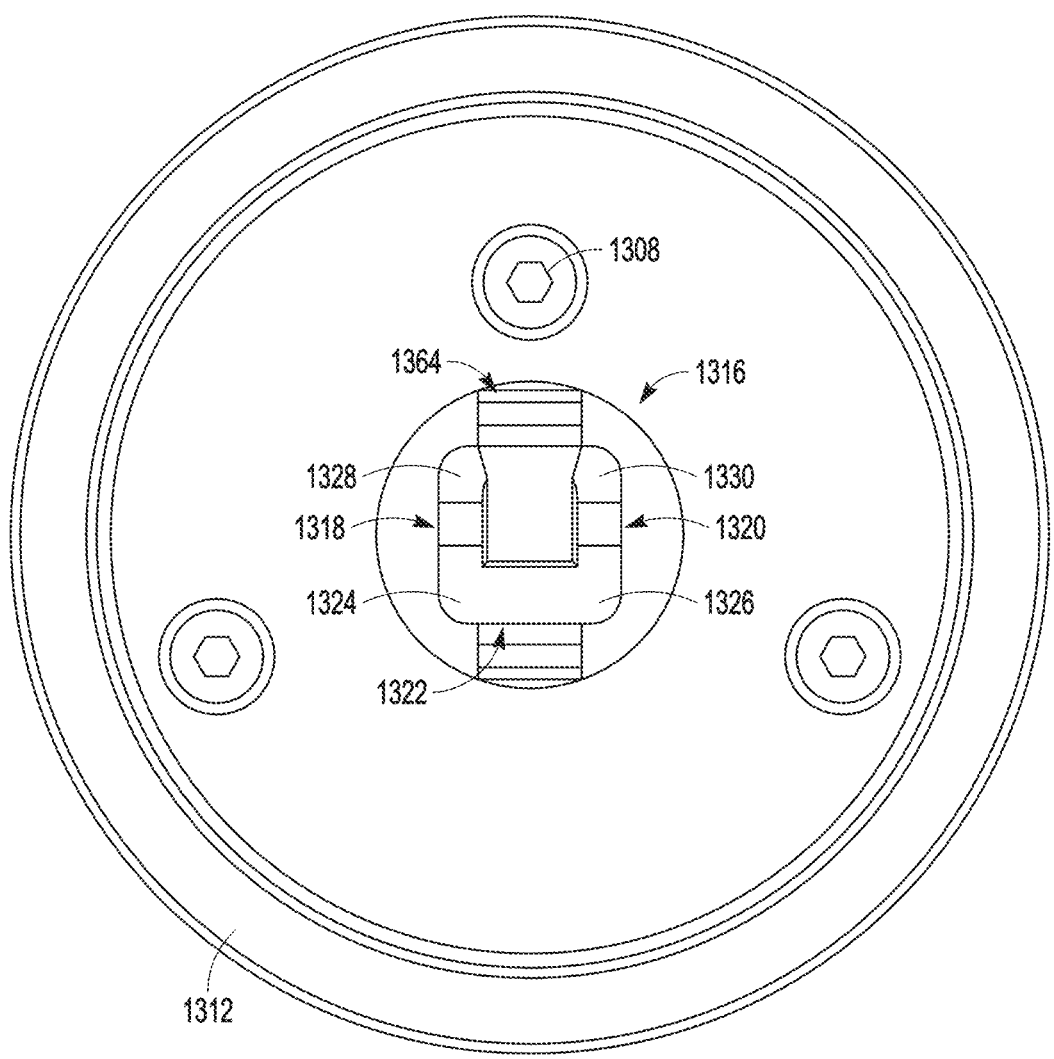

FIGS. 13A and 13B illustrate generally an alternative first portion 1302 for a quick connect according to the present subject matter, such as the quick connect 700 of FIG. 7. The first portion 1302 can include a base 1312, a rod 1314, and an interface 1316. The first portion 1302 is intended to remain fixed to the surgical robot for an extended portion of a surgical procedure such that multiple instruments can be quickly connected and disconnected from the surgical robot as the procedure progresses. The base 1312 supports the rod 1314 and connects with the arm of the surgical robot using multiple fasteners 1308. The rod 1314 extends the arm of the surgical robot and connects the interface 1316 with the base 1312.

The interface 1316 can be an extension of the rod 1314. The interface 1316 can include a dual hook-shaped structure. For example, the interface 1316 can include a first wall 1318, a second wall 1320, and a third or base wall 1322. The first wall 1318 and the second wall 1320 can extend from the rod 1314 and can be parallel with each other. The base wall 1322 can extend from the rod 1314 and can be joined with and between the first wall 1318 and the second wall 1320. The base wall 1322 can further be joined with each of the first wall 1318 and the second wall 1320 along a first edge 1324, 1326 of each of the first wall 1318 and the second wall 1320. Along the second edge 1328, 1330 of each of the first wall 1318 and the second wall 1320, the interface can include a notch 1332, 1334. The notches 1332, 1334 form the hook ends of the hooks of the dual hook-shaped structure. As can be observed from the end view of FIG. 13B, the interface 1316 can have a U-shaped cross-section.

In certain examples, the first portion can include a clip assembly 1364 employed within an opening of the walls of the rod 1314 proximate the interface 1316. The clip assembly can include hooks, a spring, and a hinge pin. When the collar (FIG. 15, 706) is positioned to cover the interface 1316, the clip assembly 1364 can apply pressure to align the collar 1306 with the aligned axis 1301 of the quick connect, can provide a holding force to resist displacing the collar 1306 from its position, and can provide a visual indication via the end of the hooks holding the end of the collar 1306 that the collar is in a proper position to secure the interface of the first and second portions of the quick connect.

Figure 14:
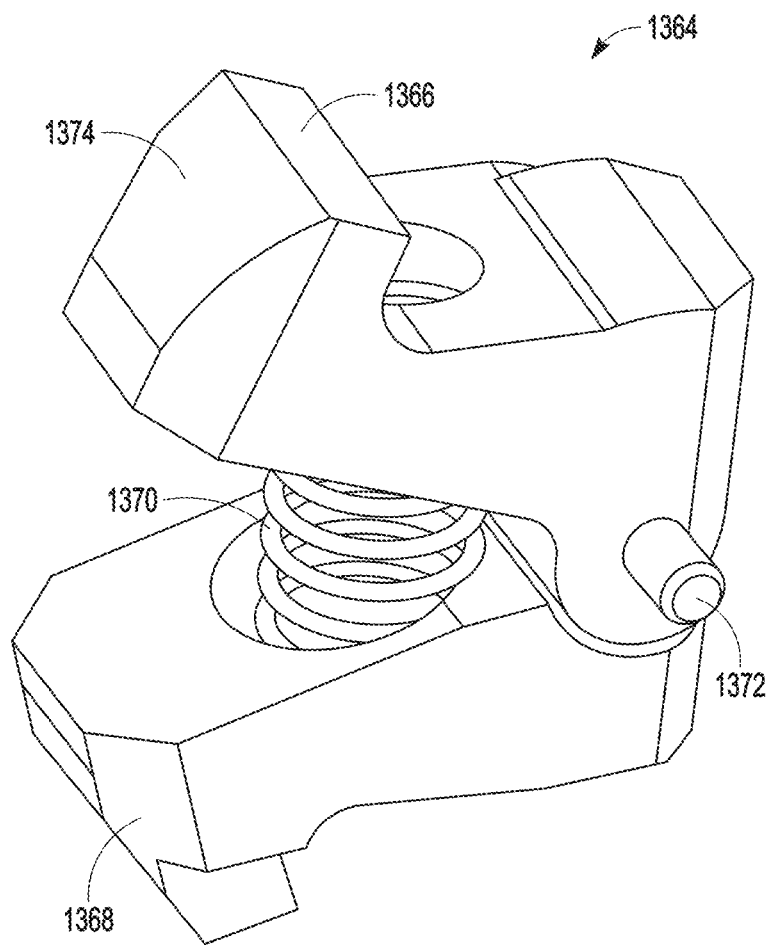
FIG. 14 illustrates generally an example of the clip assembly.

FIG. 14 illustrates generally an example of the clip assembly 1364. The clip assembly 1364 can include a first hook 1366, a second hook 1368, a spring 1370, and a hinge pin 1372. Each of the first hook 1366 and the second hook 1368 include a pair of hinge pin holes (not individually visible). The hinge pin holes of the second hook 1368 can fit within the area between the hinge pin holes of the first hook 1368 and can align such that the hinge pin 1372 can pass through all the hinge pin holes. When installed in the opening of the rod (FIG. 13A, 1314), the hinge pin 1372 can pass through a first hinge pin hole (FIG. 13A, 1376) in a first side of the rod, the pin holes of the first and second hooks 1366, 1368, and a second hinge pin hole on the opposite side of the rod. The spring 1370 can be compressed and placed in the area between the hooks 1366, 1368 and operates to separate the end of the hooks 1366, 1368 opposite the hinge pin holes.

Figure 15:
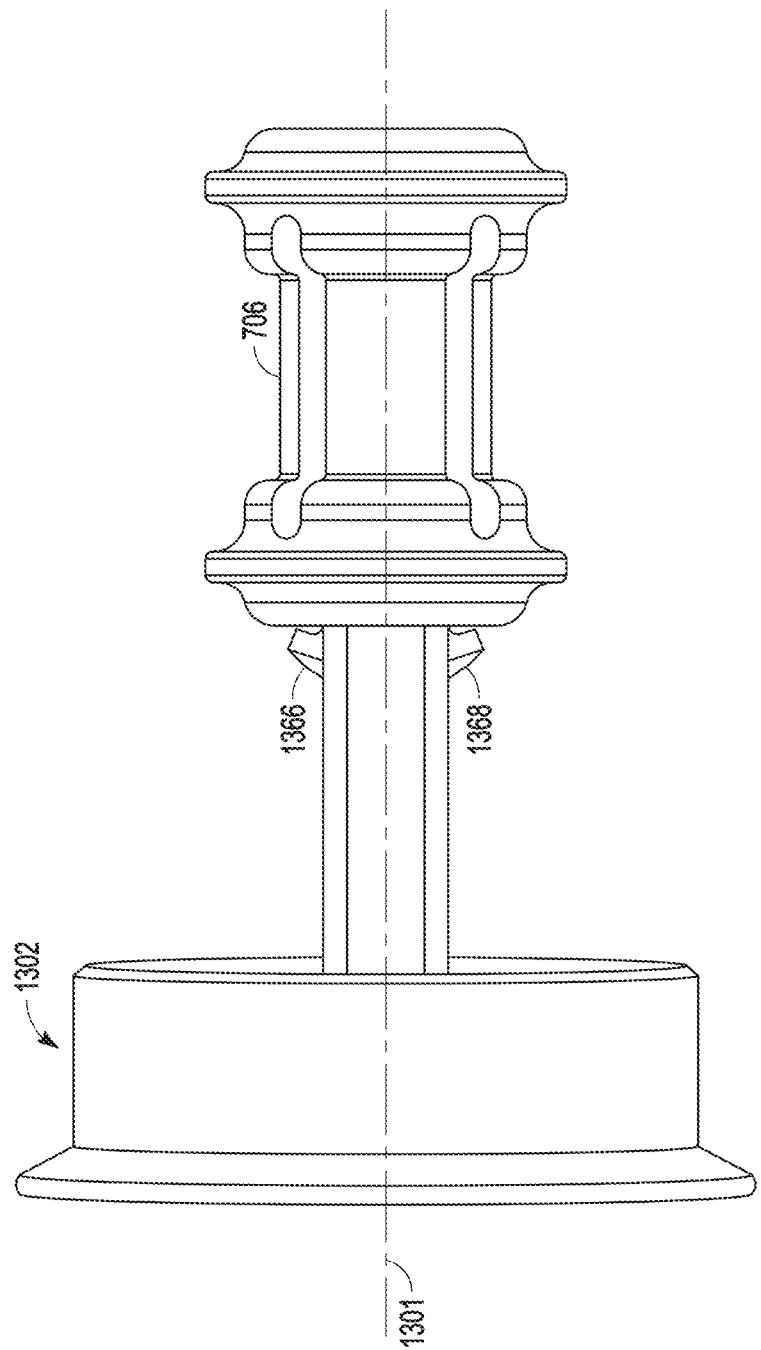
FIG. 15 illustrates a first portion of a quick connect with the collar properly positioned to secure the first portion with a second portion of the quick connect.

When the collar (FIG. 15, 706) is located in a proper position to secure the interfaces of the first and second portions of the quick connect, as shown in FIG. 15, the hook ends of the hooks 1366, 1368 can be pushed by the spring 1370 to be exposed outside the opening within the rod for the clip assembly 1364. The hook ends of the hooks 1366, 1668 can capture an end of the collar 706 to maintain the collar in the proper position. To release the collar, a user can pinch the hook end of the hooks 1366, 1368 of the clip assembly 1364 together and slide the collar over the opening in the rod for the clip assembly 1364. In certain examples, the first and second hooks 1366, 1368 can include a ramped surface 1374 that allows the thrust surface (FIG. 9, 555) or an edge of the thrust surface of the collar 506 to pinch the hooks 1366, 1368 together when the collar 506 is moved from a position about the rod of the first portion toward the position to properly secure the interfaces of the first and second portions of the quick connect.

As discussed above, FIG. 15 illustrates a first portion 1102 of a quick connect with the collar 706 properly positioned to secure the first portion 1102 with a second portion (e.g., FIG. 7, 704) (not shown in FIG. 15) of the quick connect. The proper position of the collar 706 to secure the first portion 1302 with a second portion allows the hook ends of the hooks 1366, 1368 of the clip assembly 1364 to separate from each other and capture an end of the collar 706 to limit motion of the collar 706 along the aligned axis 701 in a direction that would release the secure connection of the interfaces of the first portion 1302 and a second portion of a quick connect.

Figure 16:
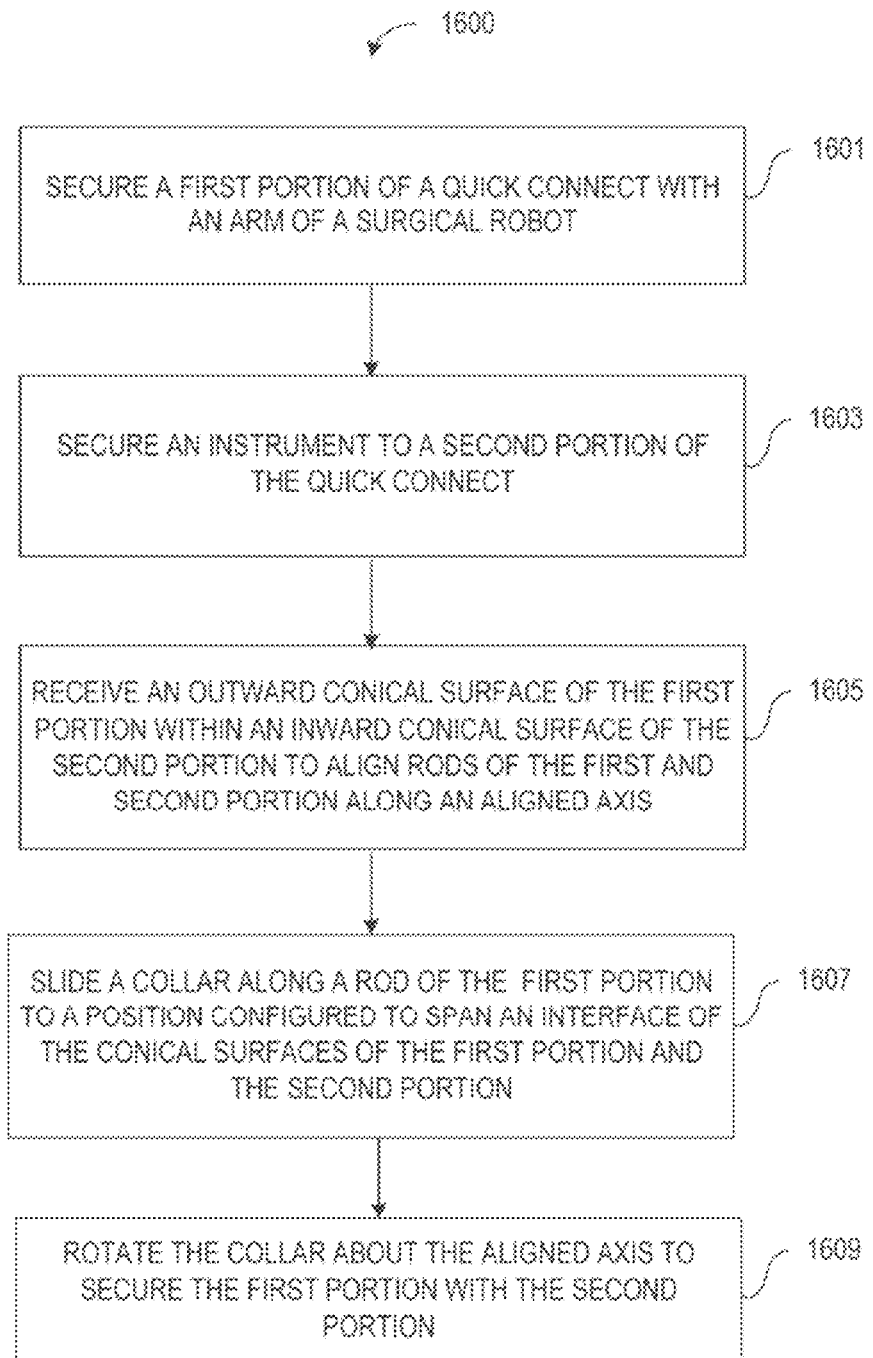
FIG. 16 illustrates generally an example method of operating a quick connect according to the present subject matter.

FIG. 16 illustrates generally an example method of operating a quick connect according to the present subject matter, such as the quick connect of FIG. 3. At 1601, a first portion of the quick connect can be secured to an arm of a surgical robot. At 1603, a surgical instrument can be secured to a second portion of the quick connect. The surgical instrument can include, but is not limited to, a resection guide. a reamer, an impactor, a drill guide, pedicle screw driver, etc. At 1605, an outward conical surface of the first portion can be received by an inward conical surface of the second portion. The conical shape of the first and second portion naturally aligns a rod of the first portion with a rod of the second portion along an aligned axis (FIG. 3, 301). At 1607, a collar can be slid along the aligned axis to span an interface of the conical surfaces of the first portion and the second portion. In certain examples, the collar is assembled to the second portion prior to the output conical portion of the first portion being received by the inward conical portion of the second portion. In certain examples, grooves of the first and second portions can guide cam followers of the collar along the aligned axis. At 1609, the collar can be rotated about the aligned axis to secure the first portion with the second portion. In certain examples, the rotation motion of the collar allows the cam followers of the collar to follow a ramped profile of the groves of the first portion that displaces the collar further along the aligned axis towards the base of the first portion. At the same time, a thrust surface of the second portion can be engaged by a thrust surface of the collar to pull the second portion to the first portion to secure the first portion tightly with the second portion.

Figure 17:
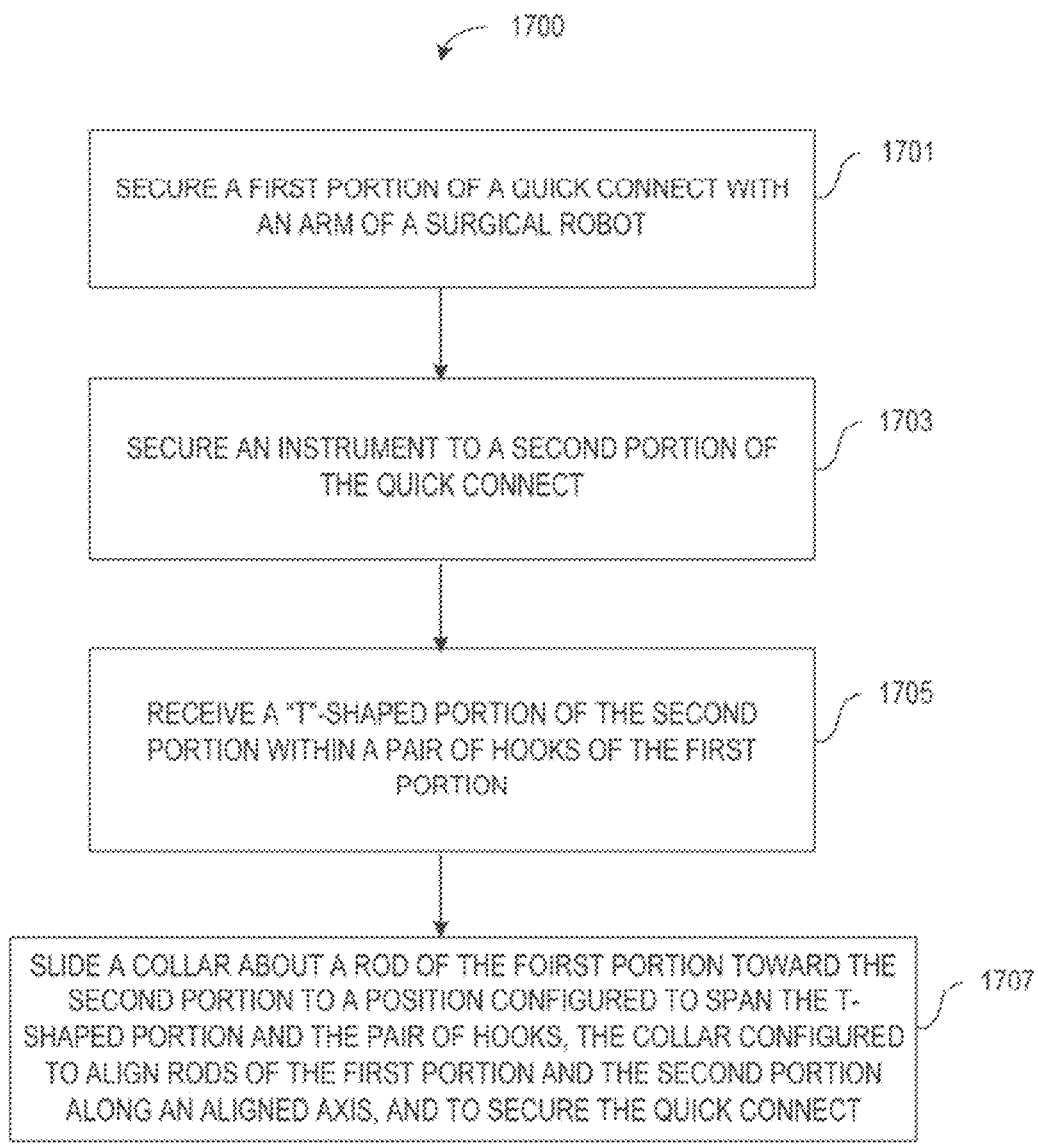
FIG. 17 illustrates generally an example method of operating a quick connect according to the present disclosure, such as the quick connect of FIGS. 7-15.

FIG. 17 illustrates generally an example method of operating a quick connect according to the present disclosure, such as the quick connect of FIGS. 7-13. At 1701, a first portion of the quick connect can be secured to an arm of a surgical robot. At 1703, a surgical instrument can be secured to a second portion of the quick connect. The surgical instrument can include, but is not limited to, a resection guide. a reamer, an impactor, a drill guide, etc. At 1705, a pair of hooks of the first portion can receive a "t"-shaped portion of the second portion. At 1707, a collar about a rod of the first portion can be slid toward the second portion to a lock position that spans the interface of the "t"-shaped portion of the second portion and the hooks of the first portion. In certain examples, the collar can be assembled onto the first portion prior to coupling the hooks of the first portion with the "t"-shaped end of the second portion. In certain examples, the lock position of the collar can align the first and second portions of the quick connect an aligned axis to secure the quick connect. In some examples, the locked position of the collar can have one or more thrust or alignment surfaces of an interface of the second portion engage with corresponding thrust or alignment surfaces of the collar. In certain examples, as the collar is slid into the locked position, an opening of the rod of the first portion of the quick connect can be exposed such that hook ends of a clip assembly can extend beyond the exterior surface of the rod. The hook ends of the clip assembly can be spring loaded and can prevent the collar from retracting from the locked position. In addition, the exposed hook ends of the clip assembly can serve as a visual indicator of whether the collar is or is not in the locked position. To remove or replace the instrument from the arm of the surgical robot, the user can pinch the hook ends together and slide an end of the collar toward the base of the first portion of the quick connect until the collar prevents the hook ends from extending past the external surface of the rod of the first portion, and until the collar exposes the interface between the hooks of the first portion and the "t"-shaped end of the second portion. One the interface is exposed, the "t"-shaped end of the second portion can be disengaged from the hooks of the first portion.

Figure 18:
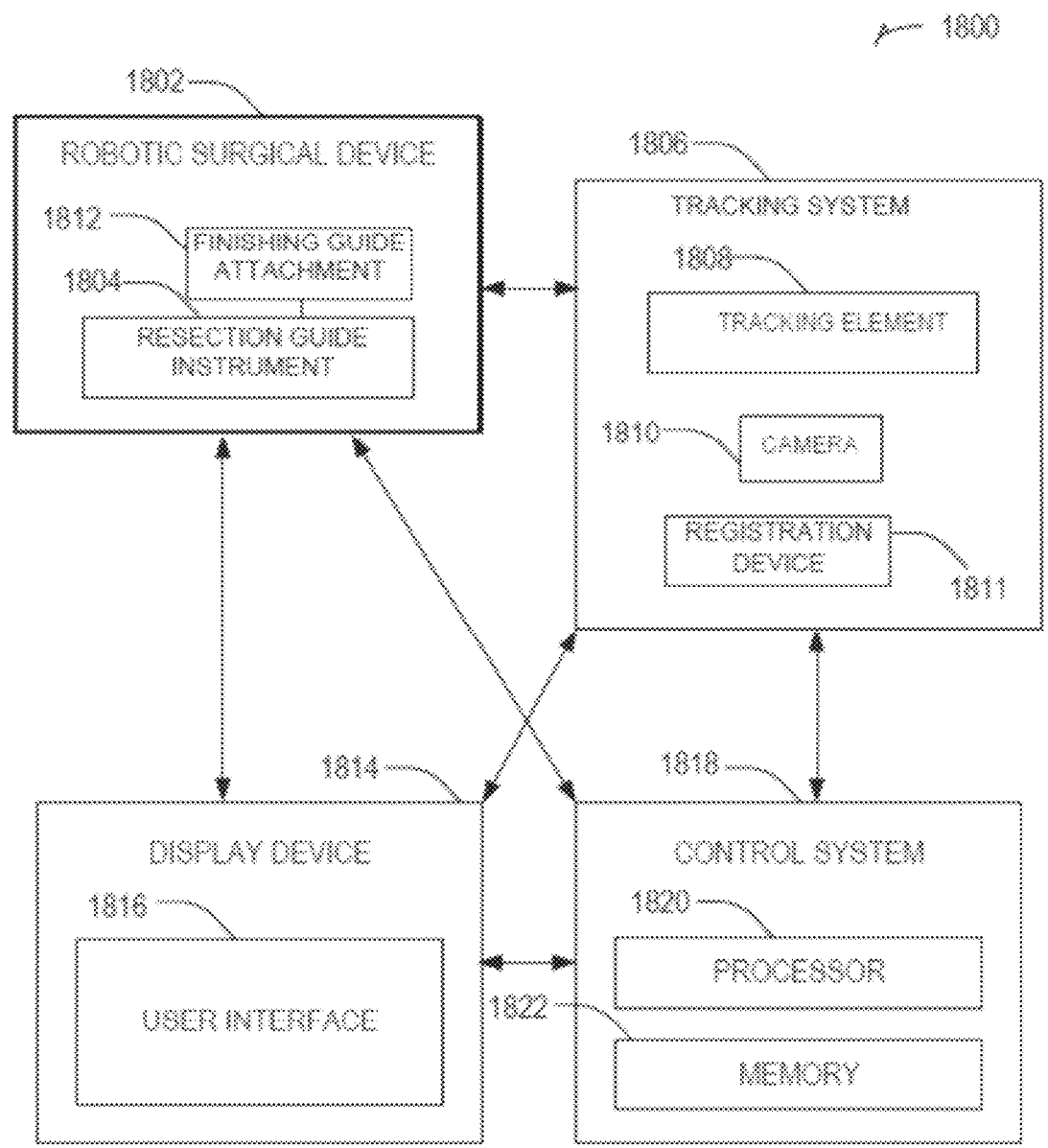
FIG. 18 illustrates system for performing techniques described herein, in accordance with some embodiments.

FIG. 18 illustrates system 1800 for performing techniques described herein, in accordance with some embodiments. System 1800 is an example of a system that can incorporate surgical system 103 of FIG. 1. System 1800 can include robotic surgical device 1802 (e.g., robotic surgical device 115) coupled to surgical instrument via a quick connect, which may interact with tracking system 1806. In other examples, the surgical instruments described herein can be used without tracking system 1806. Tracking system 1806 can include tracking element 1808, camera 1810 and registration device 1811 (e.g., pointer 326). Resection guide instrument 1804 (e.g., adapter 200) can include attachment instruments 1812. System 1800 can include display device 1814, which can be used to display user interface 1816. System 1800 can include control system 1818 (e.g., a robotic controller or computing system 140 of FIG. 1), including processor 1820 and memory 1822. In an example, display device 1814 can be coupled to one or more of robotic surgical device 1802, tracking system 1806, or control system 1818. As such, data generated by registration device 1811 can be shared with control system 1818, tracking system 1806 and an operator of system 1800 via display device 1814. In certain examples, instrument adapter 1804 can be operated without input from tracking system 1808, after a registration process, such that robotic surgical device 1802 can be positioned and tracked by movement of robotic arm 120 within the native coordinate system of robotic arm 120. Once in a desired position, a surgical instrument coupled via a quick connect can be freely used by a surgeon without tracking system 1806 required to reacquire position information for robotic surgical device and without control system 1818 losing track of the location of robotic surgical device 1802.

Figure 19:
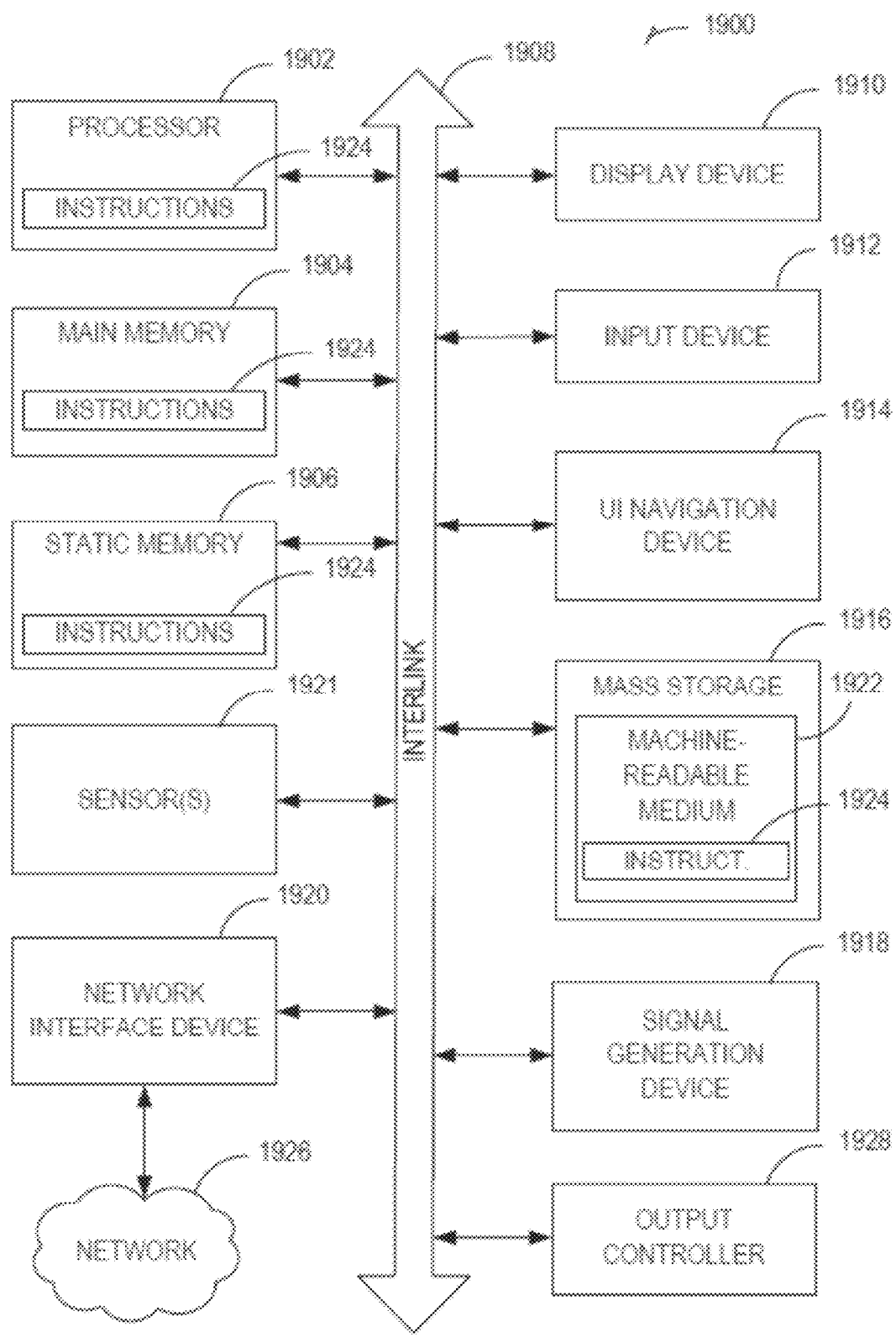
FIG. 19 illustrates a block diagram of an example machine upon which any one or more of the techniques discussed herein may be performed in accordance with some embodiments.

FIG. 19 illustrates a block diagram of an example machine 1900 upon which any one or more of the techniques discussed herein may be performed in accordance with some embodiments. For example, machine 1900 can comprise computing system 140 of FIG. 1. Machine 1900 can comprise an example of a controller for robotic system 115 and sensors 1921 can include tracking elements 190. As such instructions 1924 can be executed by processor 1902 to generate and correlate position and orientation information to determine the position and orientation of a surgical instrument coupled to the robotic arm via a quick connect and relative to robotic arm 120.

In alternative embodiments, machine 1900 may operate as a standalone device or may be connected (e.g., networked) to other machines. In a networked deployment, machine 1900 may operate in the capacity of a server machine, a client machine, or both in server-client network environments. In an example, machine 1900 may act as a peer machine in peer-to-peer (P2P) (or other distributed) network environment. Machine 1900 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1900 may include hardware processor 1902 (e.g., a central processing unit (CPU), a graphics processing unit (GPU), a hardware processor core, or any combination thereof), main memory 1904 and static memory 1906, some or all of which may communicate with each other via interlink (e.g., bus) 1908. Machine 1900 may further include display unit 1910, alphanumeric input device 1912 (e.g., a keyboard), and user interface (UI) navigation device 1914 (e.g., a mouse). In an example, display unit 1910, input device 1912 and UI navigation device 1914 may be a touch screen display. Machine 1900 may additionally include storage device (e.g., drive unit) 1916, signal generation device 1918 (e.g., a speaker), network interface device 1920, and one or more sensors 1921, such as a global positioning system (GPS) sensor, compass, accelerometer, or other sensor. Machine 1900 may include output controller 1928, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

Storage device 1916 may include machine readable medium 1922 on which is stored one or more sets of data structures or instructions 1924 (e.g., software) embodying or utilized by any one or more of the techniques or functions described herein. Instructions 1924 may also reside, completely or at least partially, within main memory 1904, within static memory 1906, or within hardware processor 1902 during execution thereof by machine 1900. In an example, one or any combination of hardware processor 1902, main memory 1904, static memory 1906, or storage device 1916 may constitute machine readable media.

While machine readable medium 1922 is illustrated as a single medium, the term "machine readable medium" may include a single medium or multiple media (e.g., a centralized or distributed database, and/or associated caches and servers) configured to store the one or more instructions 1924. The term "machine readable medium" may include any medium that is capable of storing, encoding, or carrying instructions for execution by machine 1900 and that cause machine 1900 to perform any one or more of the techniques of the present disclosure, or that is capable of storing, encoding or carrying data structures used by or associated with such instructions. Non-limiting machine readable medium examples may include solid-state memories, and optical and magnetic media.

Instructions 1924 may further be transmitted or received over communications network 1926 using a transmission medium via network interface device 1920 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 1902.11 family of standards known as Wi-Fi®, IEEE 1902.16 family of standards known as WiMax®), IEEE 1902.15.4 family of standards, peer-to-peer (P2P) networks, among others. In an example, network interface device 1920 may include one or more physical jacks (e.g., Ethernet, coaxial, or phone jacks) or one or more antennas to connect to communications network 1926. In an example, network interface device 1920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by machine 1900, and includes digital or analog communications signals or other intangible medium to facilitate communication of such software.

The systems, devices and methods discussed in the present application can be useful in performing robotic-assisted surgical procedures that utilize robotic surgical arms that can be used to position devices relative to a patient to perform arthroplasty procedures, such as partial knee arthroplasties. In particular the systems, devices and methods disclosed herein are useful in improving the accuracy with which posterior cuts and other finishing cuts on a femur are performed. The systems, devices and methods disclosed herein can reduce or eliminate the need for reliance on manually positioning of cutting guides by utilizing surgical guidance systems to orient finishing guides either directly with navigation or through positioning with a robotic surgical arm.

EXAMPLES AND NOTES

Example 1 is an apparatus for coupling a surgical instrument to a surgical robot; the apparatus comprising: a first portion configured to attach to an end of an arm of the surgical robot using a plurality of fasteners, the first portion including a first rod extending away from the arm to provide a distal end of the first portion; a second portion configured to hold the surgical instrument, the second portion including a second rod extending away from the surgical instrument to provide a distal end of the second portion; a first interface located at the distal end of the first portion; a second interface located at the distal end of the second portion, the second interface configured to join with the first interface and to align the second rod with the first rod to form an aligned axis; and a first collar configured to collar the first and second interface to secure the first portion with the second portion, and to slidably adjust along the aligned axis to allow engagement and dis-engagement of the first and second interfaces with each other.

In Example 2, the subject matter of Example 1 includes, wherein the first collar is configured to provide structural stiffness to forces exerted on the second portion at an angle to the aligned axis of the first portion and the second portion.

In Example 3, the subject matter of Examples 1-2 includes, wherein the first interface includes an outward, conically shaped alignment surface.

In Example 4, the subject matter of Example 3 includes, wherein the outward, conically shaped alignment surface is spring loaded along the aligned axis.

In Example 5, the subject matter of Examples 3-4 includes, wherein the first interface includes a second collar located between the first rod and the outward, conically shaped alignment surface.

In Example 6, the subject matter of Example 5 includes, wherein the second collar includes a first cam groove configured to receive a cam follower of the first collar.

In Example 7, the subject matter of Example 6 includes, wherein the first cam groove is configured to rotate the first collar about the aligned axis and secure the first interface with the second interface.

In Example 8, the subject matter of Examples 1-7 includes, wherein the second interface includes a receiver having an inward, conically shaped alignment surface.

In Example 9, the subject matter of Example 8 includes, wherein an outer surface of the receiver includes a first cam groove configured to receive a cam follower of the first collar and to guide the cam follower to a second cam groove of the first interface.

In Example 10, the subject matter of Example 9 includes, wherein the outer surface of the receiver includes a ramped, thrust surface configured to engage an internal thrust surface of the first collar to secure the second interface with the first interface in response to the cam follower following of the first interface.

In Example 11, the subject matter of Examples 1-10 includes, wherein the first interface includes: a first wall extending from the first rod; a second wall extending from the first rod, the second wall extending from the rod parallel with the first wall; a base wall extending with, and between, the first and second walls from the first rod, the base wall connected with a first edge of the first wall and a first edge of the second wall; wherein a second edge of the first wall includes a first notch; and wherein a second edge of the second wall includes a second notch, the first and second notch aligned with each other a distance from a distal end of each of the first wall, the second wall and the base wall.

In Example 12, the subject matter of Example 11 includes, wherein the first interface includes multiple ball detents configured to exert pressure to an interior surface of the first collar.

In Example 13, the subject matter of Examples 11-12 includes, wherein the first rod includes a scissor hook assembly anchored inside the first rod and extending outside the first rod.

In Example 14, the subject matter of Example 13 includes, wherein the scissor hook assembly provides a visual cue for an engagement status of the first collar.

In Example 15, the subject matter of Examples 13-14 includes, wherein the notch of the first wall includes a first edge, a second edge and a third edge; wherein the second edge of the notch extends parallel the first edge of the first wall; wherein the first edge of the notch connects the second edge of the first wall with the first edge of the notch proximal the first rod; and wherein the third edge of the notch connects the second edge of the first rod with the first edge of the notch proximal the distal end of the first interface opposite the first rod.

In Example 16, the subject matter of Examples 13-15 includes, wherein the second interface includes a post extending from the second rod along the aligned axis; a first nub extending from the post parallel to the aligned axis; a second nub extending from the post opposite the first nub and parallel to the aligned axis; wherein the first interface is configured to receive the post between the first wall and the second wall; wherein the notch of the first wall is configured to receive the first nub; and wherein the notch of the second wall is configured to receive the second nub.

In Example 17, the subject matter of Example 16 includes, wherein the second interface includes a ramped thrust surface coupling the post with the second rod, and wherein the ramped thrust surface is configured to engage with a first thrust surface of the first collar in response to the first collar positioned to secure engagement of the first interface with the second interface.

In Example 18, the subject matter of Example 17 includes, wherein the first collar includes: the first thrust surface at a first end; a second thrust surface at a second; and wherein the first thrust surface and the second thrust surface allow the first collar to be assembled with the apparatus in either of two ways.

Example 19 is a method for connecting an instrument to an arm of a surgical robot, the method comprising: securing a first portion of a connector with the arm; securing the instrument with a second portion of the connector; receiving an outward conical surface of the first portion within an inward conical surface of the second portion to align the first portion and the second portion along an axis to provide an aligned axis; sliding a collar positioned about a rod of the second portion toward the first portion to cover an interface of the outward conical portion surface and the inward conical portion; and rotating the collar about the aligned axis to secure the first portion with the second portion.

In Example 20, the subject matter of Example 19 includes, sliding the collar includes sliding a cam follower within a groove of the second portion, the groove of the second portion extending parallel with the aligned axis.

In Example 21, the subject matter of Example 20 includes, wherein rotating the collar includes sliding the cam follower in a groove of the first portion.

In Example 22, the subject matter of Example 21 includes, wherein the groove of the first portion is configured to engage a surface of the second portion with an interior surface of the collar and to apply force on the second portion in a direction of the first portion.

In Example 23, the subject matter of Examples 19-22 includes, acquiring first position information of the instrument at a control system; using the instrument to perform a first portion of a procedure; tracking a position of the instrument during the first portion of the procedure at a control system; replacing the second portion with a different second portion, the different second portion including a second instrument; continuing the procedure with the second instrument; and tracking a position of the second instrument at the control system without acquiring second position information of the second instrument.

Example 24 is a method for connecting an instrument to an arm of a surgical robot, the method comprising: securing a first portion of a connector with the arm; securing the instrument within a second portion of the connector; receiving a "t"-shaped portion of the second portion within a pair of hooks of the first portion; aligning a rod of the first portion with a rod of the second portion along an axis to provide an aligned axis; and sliding a collar positioned about the rod of the first portion toward the second portion to span an interface of the "t"-shaped portion and the pair of hooks.

In Example 25, the subject matter of Example 24 includes, sliding the collar to engage an internal alignment surface of the collar with an exterior alignment surface of the second portion.

In Example 26, the subject matter of Examples 24-25 includes, wherein sliding the collar to engage includes exposing a port of the first portion; and allowing an end of a scissor assembly to pass through the port to provide a visual indication of connection of the first portion and the second portion.

In Example 27, the subject matter of Example 26 includes, wherein the scissor assembly is configured to prevent the collar from sliding toward the arm.

In Example 28, the subject matter of Examples 25-27 includes, acquiring first position information of the instrument at a control system; using the instrument to perform a first portion of a procedure; tracking a position of the instrument during the first portion of the procedure at a control system; replacing the second portion with a different second portion, the different second portion including a second instrument; continuing the procedure with the second instrument; and tracking a position of the second instrument at the control system without acquiring second position information of the second instrument.

Example 29 is at least one machine-readable medium including instructions that, when executed by processing circuitry, cause the processing circuitry to perform operations to implement of any of Examples 1-28.

Example 30 is an apparatus comprising means to implement of any of Examples 1-28.

Example 31 is a system to implement of any of Examples 1-28.

Example 32 is a method to implement of any of Examples 1-28.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. The Abstract is provided to comply with 37 C.F.R. § 1.72(b), to allow the reader to quickly ascertain the nature of the technical disclosure. It is submitted with the understanding that it will not be used to interpret or limit the scope or meaning of a claim. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment.

What is claimed is:

1. An apparatus for coupling a surgical instrument to a surgical robot;
   the apparatus comprising:
   a first portion configured to attach to an end of an arm of the surgical robot using a plurality of fasteners, the first portion including a first rod extending away from the arm to provide a distal end of the first portion;
   a second portion configured to hold the surgical instrument, the second portion including a second rod extending away from the surgical instrument to provide a distal end of the second portion;
   a first interface located at the distal end of the first portion;
   a second interface located at the distal end of the second portion, the second interface including a receiver having an inward, conically shaped alignment surface and configured to join with the first interface and to align the second rod with the first rod to form an aligned axis; and
   a first collar configured to collar the first and second interface to secure the first portion with the second portion, and to slidably adjust along the aligned axis to allow engagement and dis-engagement of the first and second interfaces with each other, wherein an outer surface of the receiver includes a first cam groove configured to receive a cam follower of the first collar and to guide the cam follower to a second cam groove of the first interface.

2. The apparatus of claim 1, wherein the first collar is configured to provide structural stiffness to forces exerted on the second portion at an angle to the aligned axis of the first portion and the second portion.

3. The apparatus of claim 1, wherein the first interface includes an outward, conically shaped alignment surface.

4. The apparatus of claim 3, wherein the outward, conically shaped alignment surface is spring loaded along the aligned axis.

5. The apparatus of claim 3, wherein the first interface includes a second collar located between the first rod and the outward, conically shaped alignment surface.

6. The apparatus of claim 5, wherein the second collar includes a first cam groove configured to receive a cam follower of the first collar.

7. The apparatus of claim 6, wherein the first cam groove is configured to rotate the first collar about the aligned axis and secure the first interface with the second interface.

8. The apparatus of claim 1, wherein the outer surface of the receiver includes a ramped, thrust surface configured to engage an internal thrust surface of the first collar to secure the second interface with the first interface in response to the cam follower following of the first interface.

9. A method for connecting an instrument to an arm of a surgical robot, the method comprising:
securing a first portion of a connector with the arm;
securing the instrument with a second portion of the connector;
receiving an outward conical surface of the first portion within an inward conical surface of the second portion to align the first portion and the second portion along an axis to provide an aligned axis and receiving;
sliding a collar positioned about a rod of the second portion toward the first portion to cover an interface of the outward conical portion surface and the inward conical portion, wherein the collar includes a cam follower sliding through a first cam groove in an outer surface of the second portion into a second cam groove disposed in an outer surface of the first portion; and
rotating the collar about the aligned axis to secure the first portion with the second portion, wherein the rotating includes moving the cam follower within the second cam groove.

10. An apparatus for coupling a surgical instrument to a surgical robot;
the apparatus comprising:
a first portion configured to attach to an end of an arm of the surgical robot using a plurality of fasteners, the first portion including a first rod extending away from the arm to provide a distal end of the first portion;
a second portion configured to hold the surgical instrument, the second portion including a second rod extending away from the surgical instrument to provide a distal end of the second portion;
a first interface located at the distal end of the first portion, the first interface including an outward, conically shaped alignment surface and a second collar located between the first rod and the outward, conically shaped alignment surface;
a second interface located at the distal end of the second portion, the second interface configured to join with the first interface and to align the second rod with the first rod to form an aligned axis; and
a first collar configured to collar the first and second interface to secure the first portion with the second portion, and to slidably adjust along the aligned axis to allow engagement and dis-engagement of the first and second interfaces with each other, wherein the second collar includes a first cam groove configured to receive a cam follower of the first collar.

11. The apparatus of claim 10, wherein the first collar is configured to provide structural stiffness to forces exerted on the second portion at an angle to the aligned axis of the first portion and the second portion.

12. The apparatus of claim 10, wherein the outward, conically shaped alignment surface is spring loaded along the aligned axis.

13. The apparatus of claim 10, wherein the first cam groove is configured to rotate the first collar about the aligned axis and secure the first interface with the second interface.

14. The apparatus of claim 10, wherein the second interface includes a receiver having an inward, conically shaped alignment surface.

15. The apparatus of claim 14, wherein an outer surface of the receiver includes a first cam groove configured to receive a cam follower of the first collar and to guide the cam follower to a second cam groove of the first interface.

16. The apparatus of claim 15, wherein the outer surface of the receiver includes a ramped, thrust surface configured to engage an internal thrust surface of the first collar to secure the second interface with the first interface in response to the cam follower following of the first interface.

* * * * *